US010816461B2

(12) United States Patent
Mizuuchi et al.

(10) Patent No.: US 10,816,461 B2
(45) Date of Patent: Oct. 27, 2020

(54) GAS SENSOR AND CONSTANT-TEMPERATURE APPARATUS

(71) Applicant: PHC HOLDINGS CORPORATION, Tokyo (JP)

(72) Inventors: Kiminori Mizuuchi, Osaka (JP); Masaki Yamamoto, Ehime (JP); Akira Sakaguchi, Gunma (JP); Hidenori Watanabe, Tochigi (JP); Tomoyoshi Tokumaru, Gunma (JP); Tsugumasa Hitomi, Gunma (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 121 days.

(21) Appl. No.: 16/160,597

(22) Filed: Oct. 15, 2018

(65) Prior Publication Data

US 2019/0049370 A1 Feb. 14, 2019

Related U.S. Application Data

(63) Continuation of application No. PCT/JP2017/015092, filed on Apr. 13, 2017.

(30) Foreign Application Priority Data

Apr. 15, 2016 (JP) .................................. 2016-082426
Aug. 26, 2016 (JP) .................................. 2016-166233

(51) Int. Cl.
*G01N 21/3504* (2014.01)
*G01N 21/09* (2006.01)
(Continued)

(52) U.S. Cl.
CPC ......... *G01N 21/3504* (2013.01); *C12M 41/14* (2013.01); *G01N 21/05* (2013.01);
(Continued)

(58) Field of Classification Search
CPC .... G01N 21/3504; G01N 21/09; G01N 21/05; G01N 21/8507; G01N 2021/0382;
(Continued)

(56) References Cited

U.S. PATENT DOCUMENTS 4,011,451 A * 3/1977 Nelson .................. G01N 21/05
250/343
4,651,004 A * 3/1987 Uno .................... G01N 21/3504
250/343
(Continued)

FOREIGN PATENT DOCUMENTS

EP 2711688 A1 3/2014
GB 2391310 A 2/2004
(Continued)

OTHER PUBLICATIONS

International Search Report issued in corresponding International Patent Application No. PCT/JP2017/015092, dated Jun. 27, 2017, with English Translation.
(Continued)

*Primary Examiner* — Hwa Andrew Lee
(74) *Attorney, Agent, or Firm* — McDermott Will & Emery LLP

(57) ABSTRACT

A gas sensor includes: a gas detection unit including a light source and a detector; and a gas passage including a first end, a second end and a hollow part. The hollow part has a shape in which a cross-sectional area of a flow passage grows smaller. The gas passage includes: a member that divides the hollow part into at least a first area and a second area; a gas inflow port; and a gas outflow port. The gas flows from the gas inflow port into the hollow part, flows in the first area to arrive at the gas detection unit, and the gas located in the gas detection unit flows in the second area and flows out from the gas outflow port.

10 Claims, 20 Drawing Sheets

(51) Int. Cl.
  *G01N 21/05* (2006.01)
  *C12M 1/00* (2006.01)
  *G01N 21/85* (2006.01)
  *A61L 2/04* (2006.01)
  *G01N 21/03* (2006.01)
  *G01N 21/15* (2006.01)
  *A61L 2/26* (2006.01)

(52) U.S. Cl.
  CPC ......... *G01N 21/09* (2013.01); *G01N 21/8507* (2013.01); *A61L 2/04* (2013.01); *A61L 2/26* (2013.01); *A61L 2202/14* (2013.01); *G01N 2021/0382* (2013.01); *G01N 2021/158* (2013.01); *G01N 2021/8557* (2013.01); *G01N 2201/0636* (2013.01)

(58) Field of Classification Search
  CPC ..... G01N 2021/158; G01N 2021/8557; G01N 2201/0636; C12M 41/14; A61L 2/04; A61L 2202/14; A61L 2/26
  See application file for complete search history.

(56) References Cited

U.S. PATENT DOCUMENTS

| | | | |
|---|---|---|---|
| 5,550,375 A | 8/1996 | Peters et al. | |
| 6,307,204 B1* | 10/2001 | Kanomata | G01N 21/05 250/373 |
| 10,254,222 B2* | 4/2019 | Yasuda | G01N 21/3504 |
| 2005/0163662 A1* | 7/2005 | Mueller | G01N 21/05 422/68.1 |
| 2007/0145275 A1* | 6/2007 | Wong | G01N 21/39 250/339.13 |
| 2008/0035848 A1* | 2/2008 | Wong | G01J 3/108 250/345 |
| 2016/0054285 A1 | 2/2016 | Freese et al. | |
| 2016/0061704 A1 | 3/2016 | Deguchi et al. | |

FOREIGN PATENT DOCUMENTS

| | | |
|---|---|---|
| JP | 08-114501 A | 5/1996 |
| JP | 09-184803 A | 7/1997 |
| JP | 09-229858 A | 9/1997 |
| JP | 10-332585 A | 12/1998 |
| JP | 2012-215396 A | 11/2012 |

OTHER PUBLICATIONS

Extended European Search Report issued in corresponding European Patent Application No. 17782461.2, dated Feb. 12, 2019.

* cited by examiner

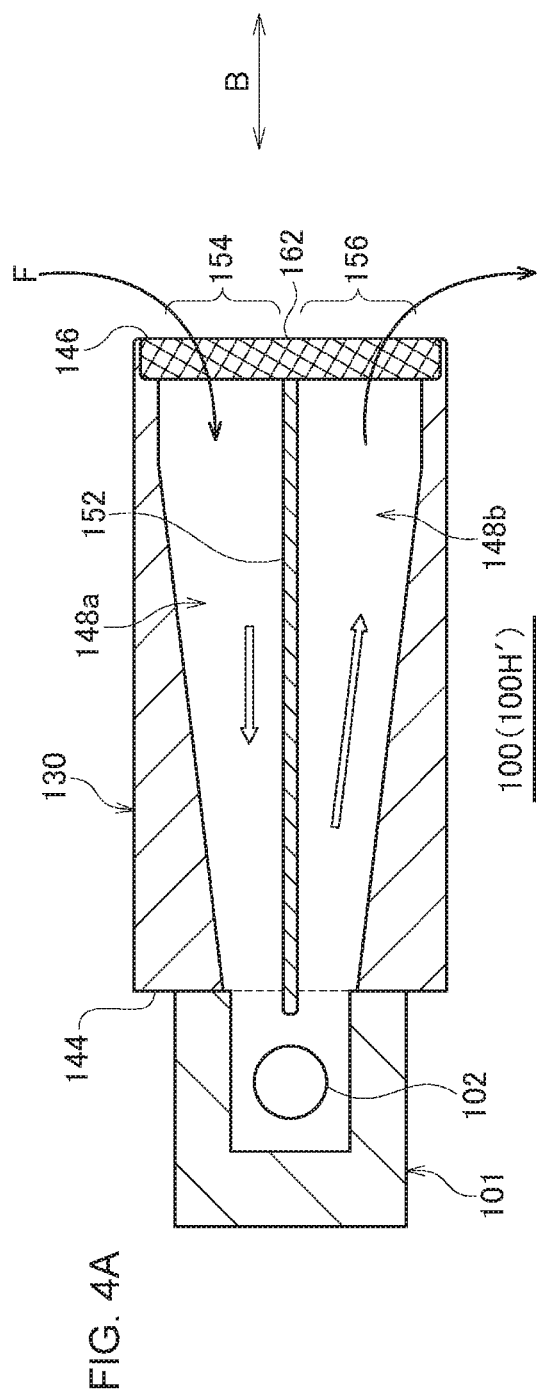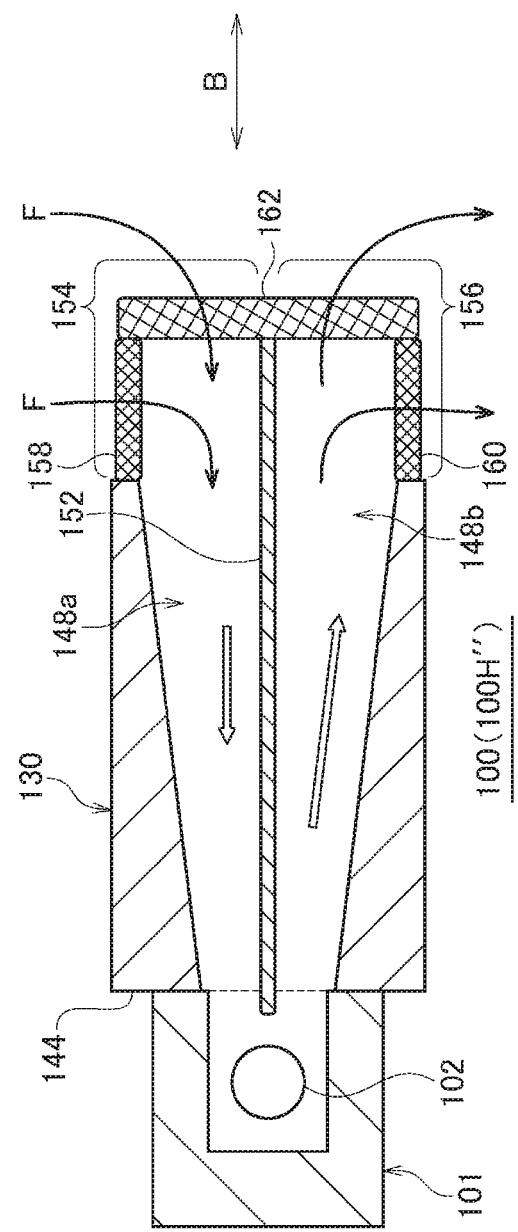

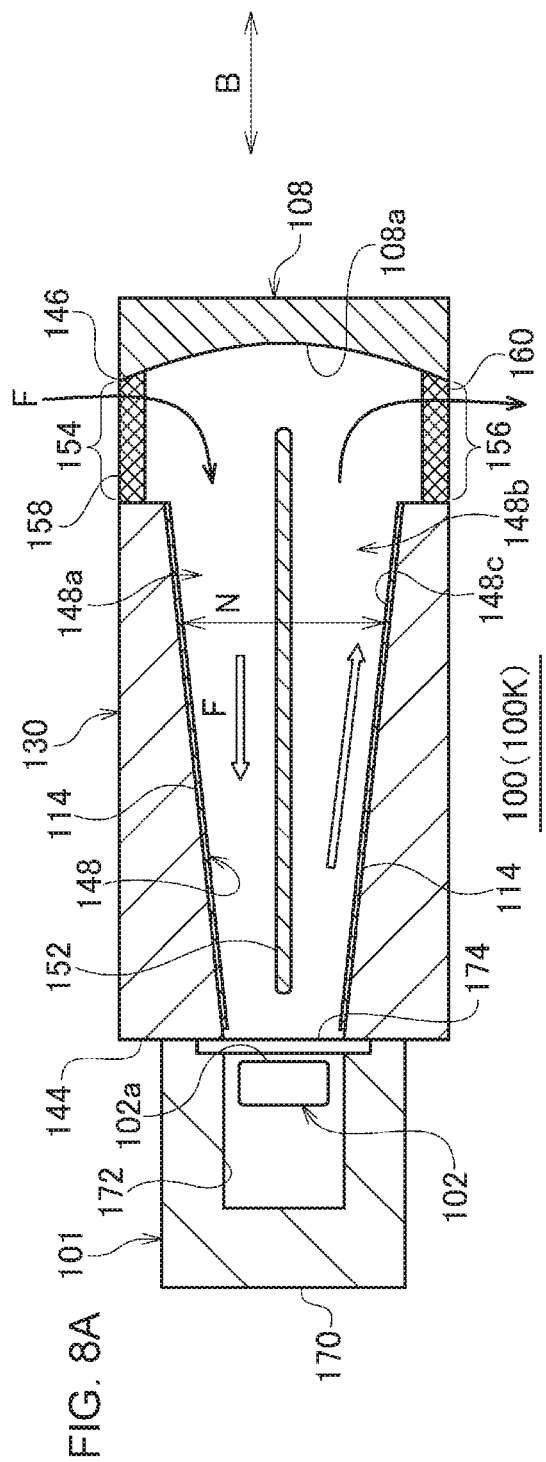
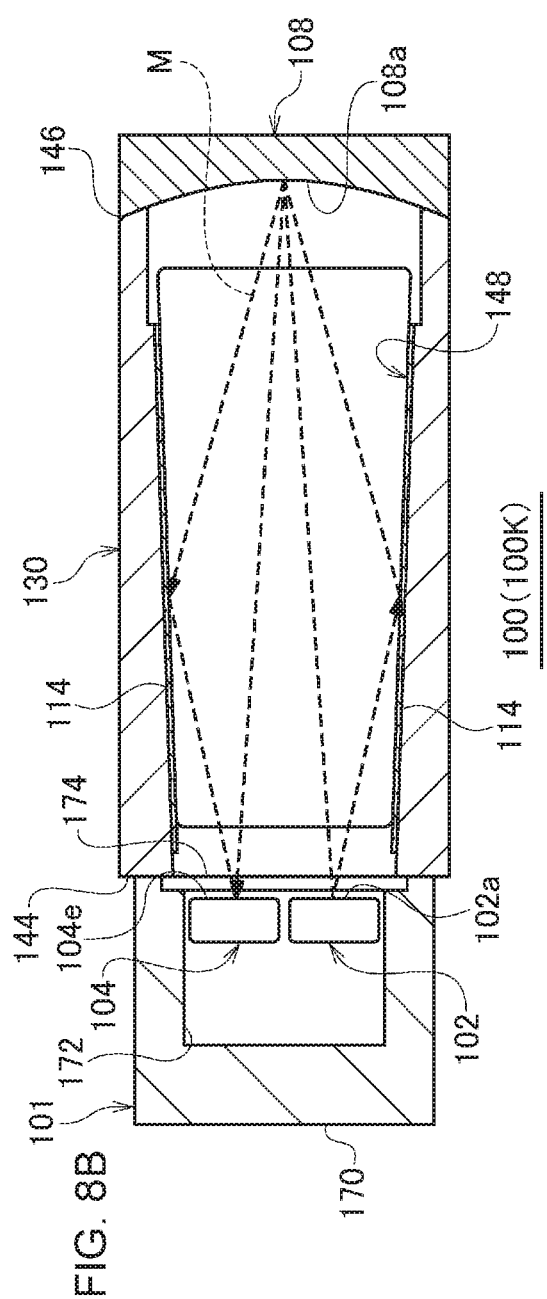

100 (100E)

GAS SENSOR AND CONSTANT-TEMPERATURE APPARATUS

CROSS-REFERENCE TO RELATED APPLICATIONS

This application is a Continuation of International Patent Application No. PCT/JP2017/015092, filed on Apr. 13, 2017, which claims benefit of priority from Japanese Patent Application No. 2016-082426, filed on Apr. 15, 2016 and Japanese Patent Application No. 2016-166233, filed on Aug. 26, 2016, the entire content of each are incorporated herein in their entirety by reference.

BACKGROUND

Field of the Invention

The present invention relates to a gas sensor and a constant-temperature apparatus provided with the gas sensor.

Description of the Related Art

Gas sensors capable of detecting a gas such as $CO_2$ and $NO_x$ are known in the related art. By way of example of such a gas sensor, patent document 1 discloses an infrared gas sensor capable of detecting the density of a gas subject to detection by using the absorption of infrared light by the gas subject to detection.

More specifically, the infrared gas sensor is provided with an infrared light source, an infrared sensor as a detector, and a reflecting plate. The infrared light source and the infrared sensor face the reflecting plate and are arranged such that the infrared light emitted from the infrared light source is reflected by the reflecting plate and arrives at the infrared sensor. Also, the infrared gas sensor is configured such that a gas subject to detection is introduced into a space between the infrared light source/infrared sensor and the reflecting plate. Therefore, the infrared light emitted from the infrared light source is absorbed in part by the gas subject to detection before arriving at the infrared sensor. The infrared gas sensor is capable of detecting the density of the gas subject to detection based on the variation in the intensity of infrared light.

Patent document 1: JP2012-215396

The gas sensor according to the related art described above is structured such that the light source and the detector are exposed to the gas subject to detection. Meanwhile, the temperature that the light source and the detector used in a gas sensor can withstand is generally about 100° C. For this reason, the temperature of the gas subject to detection may exceed the withstand temperature of the light source and the detector and lower the accuracy of detection by the gas sensor. Further, where the related-art gas sensor is mounted in a constant-temperature apparatus such as an incubator, the temperature in a space that houses the gas subject to detection may exceed the withstand temperature of the light source and the detector when the constant-temperature apparatus is sterilized by dry sterilization. In this case, the light source and the detector will be exposed to a high temperature and the accuracy of detection by the gas sensor may be lowered.

SUMMARY OF THE INVENTION

The embodiments address the above-described issues, and a general purpose thereof is to provide a technology of inhibiting the accuracy of detection by the gas sensor from being lowered.

An embodiment that addresses the above issue relates to a gas sensor. The gas sensor includes: a gas detection unit that includes a light source configured to emit light of a predetermined wavelength toward a gas subject to detection, and a detector that receives the light and detects the gas subject to detection based on absorption of the light by the gas subject to detection; and a gas passage that includes a first end, a second end opposite to the first end, and a hollow part extending from the first end to the second end, the first end being provided toward the gas detection unit, the second end being provided toward a gas space where the gas subject to detection is located, and the gas passage being configured to communicate the gas subject to detection between the gas space and the gas detection unit via the hollow part. The hollow part has a shape in which a cross-sectional area of a flow passage grows smaller away from the second end and toward the first end either in steps or continuously. The gas passage includes: a partition member that divides the hollow part into at least two areas including a first area and a second area each extending from the first end to the second end; a gas inflow port provided at the second end to connect the gas space to the first area; and a gas outflow port provided at the second end to connect the second area to the gas space. The gas subject to detection located in the gas space flows from the gas inflow port into the hollow part, flows in the first area toward the first end, and arrives at the gas detection unit, and the gas subject to detection located in the gas detection unit flows in the second area toward the second end and flows out from the gas outflow port to the gas space.

Another embodiment relates to a gas sensor. The gas sensor includes: a light source configured to emit light of a predetermined wavelength; a detector that detects a gas subject to detection based on absorption of the light by the gas subject to detection; a light passage that includes a first end and a second end opposite to the first end, the light source and the detector being provided toward the first end, and the light passage transmitting the light; a light reflecting part provided at the second end of the light passage so as to sandwich the gas space where the gas subject to detection is located. The light emitted from the light source arrives at the light reflecting part via the light passage and the gas space, is reflected by the light reflecting part, and arrives at the detector via the gas space and the light passage.

Another embodiment relates to a constant-temperature apparatus. The constant-temperature apparatus includes a constant-temperature tank that houses a gas; and the gas sensor according to the above embodiments, and the gas sensor detects the gas in the constant-temperature tank.

BRIEF DESCRIPTION OF DRAWINGS

Embodiments will now be described, by way of example only, with reference to the accompanying drawings which are meant to be exemplary, not limiting, and wherein like elements are numbered alike in several Figures, in which:

FIG. 4A is a perpendicular cross-sectional view schematically showing a gas sensor according to variation 1;

FIG. 4B is a perpendicular cross-sectional view schematically showing a gas sensor according to variation 2;

FIG. 8A is a perpendicular cross-sectional view schematically showing a gas sensor according to embodiment 5;

FIG. 8B is a horizontal cross-sectional view schematically showing the gas sensor according to embodiment 5;

FIG. 19B is a side view schematically showing the detectors and optical filters that the gas sensor according to embodiment 11 is provided with.

DETAILED DESCRIPTION OF THE INVENTION

Hereinafter, the present invention will be described based on preferred embodiments with reference to the accompanying drawings. The preferred embodiments do not intend to limit the scope of the invention but exemplify the invention. Not all of the features and the combinations thereof described in the embodiments are necessarily essential to the invention. Like numerals represent like elements so that the description will be omitted accordingly. The scales and shapes shown in the figures are defined for convenience's sake to make the explanation easy and shall not be interpreted limitatively unless otherwise specified. Terms like "first", "second", etc. used in the specification and claims do not indicate an order or importance by any means and are used to distinguish a certain feature from the others.

Embodiment 1

Figure 1:
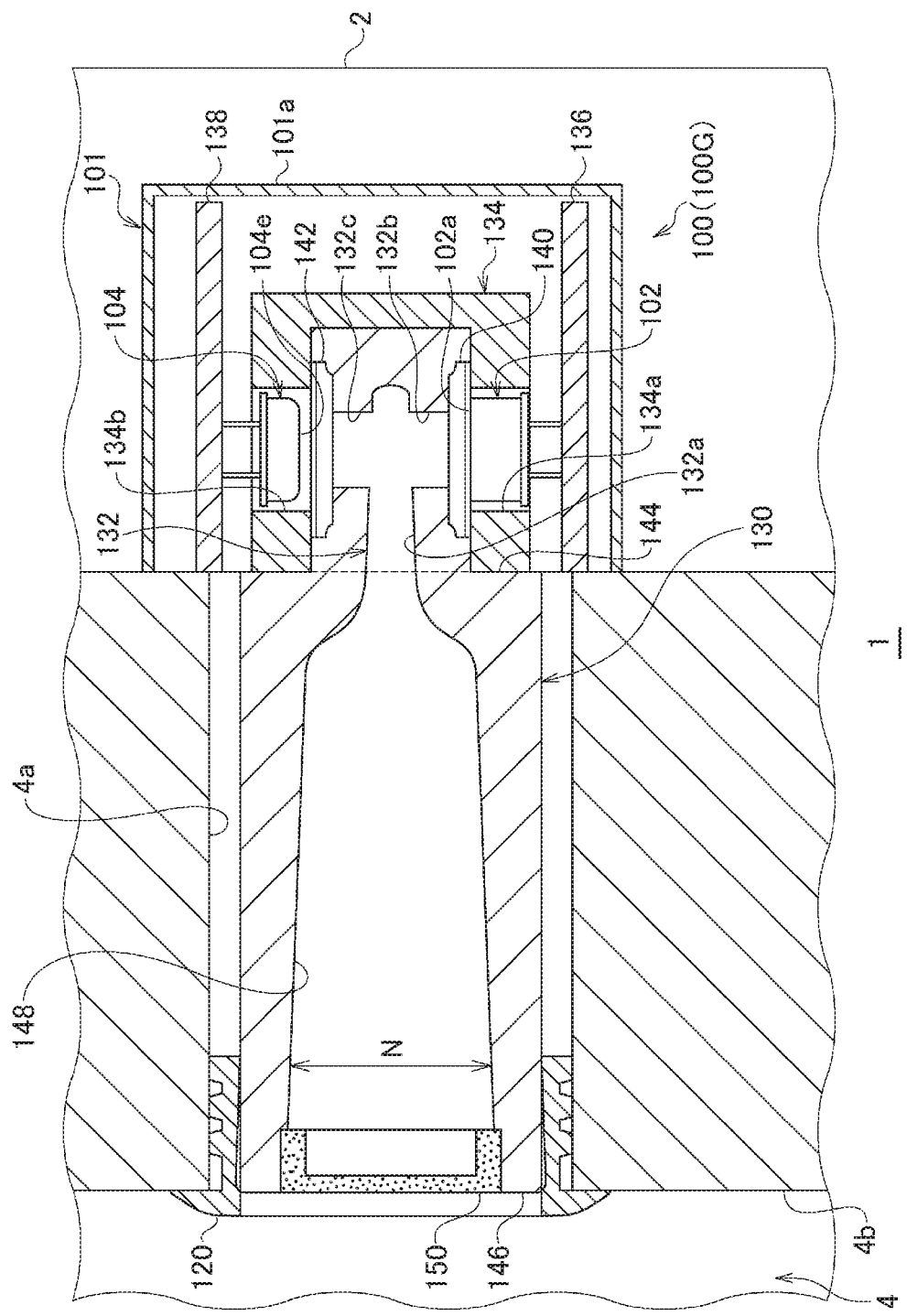
FIG. 1 is a horizontal cross-sectional view showing a part of a constant-temperature apparatus according to embodiment 1.

FIG. 1 is a horizontal cross-sectional view showing a part of a constant-temperature apparatus according to embodiment 1. FIG. 1 shows a cross-sectional shape of a gas sensor 100 observed from above in a perpendicular direction.

The constant-temperature apparatus 1 according to this embodiment is provided with a casing 2, a constant-temperature tank 4, and a gas sensor 100 (100G). The constant-temperature apparatus 1 according to this embodiment is exemplified by a $CO_2$ incubator provided with a dry-heat sterilization function. The casing 2 forms the outer casing of the constant-temperature apparatus 1. The constant-temperature tank 4 is provided inside the casing 2. The constant-temperature tank 4 houses a culture such as cells. The constant-temperature apparatus 1 is configured such that the culture can be transported into or retrieved from the constant-temperature tank 4 via an outer door (not shown) provided in the casing 2 and an inner door (not shown) provided in the constant-temperature tank 4. The constant-temperature tank 4 houses a gas (hereinafter, referred to as a tank gas) containing carbon dioxide ($CO_2$), etc.

The gas sensor 100 is a sensor for detecting a predetermined gas (hereinafter, referred to as a gas subject to detection) contained in the tank gas in the constant-temperature tank 4. The gas subject to detection in this embodiment is exemplified by $CO_2$. The gas sensor 100 is capable of detecting the presence and density of the gas subject to detection. The gas sensor 100 transmits a signal indicating the result of detection to the controller (not shown) of the constant-temperature apparatus 1. The gas sensor 100 is inserted into and fixed in a through hole 4a that communicates spaces inside and outside the constant-temperature tank 4. An adiabatic material (not shown) is provided in the space between the casing 2 and the constant-temperature tank 4.

The gas sensor 100 is provided with a gas detection unit 101 and a gas passage 130. The gas detection unit 101 includes a light source 102, a detector 104, a gas introduction chamber 132, and a bracket 134. The light source 102, the detector 104, the gas introduction chamber 132, and the bracket 134 are housed in a casing 101a.

The light source 102 emits light of a predetermined wavelength. The light source 102 according to this embodiment is exemplified by a thermal infrared light source comprised of a black-body coating and emits infrared light over an extensive wavelength range. A thermal infrared light source that emits infrared light from a high-temperature heat generator is a mainstream infrared light source. Examples of the heat generator include a filament, a ceramic, and a thin film. An LED may be used in the light source 102. The light source 102 is mounted on a substrate 136 and is electrically connected to a wiring pattern (not shown) on the substrate 136.

The detector 104 receives the light from the light source 102 and detects the gas subject to detection based on absorption of light by the gas subject to detection. More specifically, a light receiving device (not shown) of the detector 104 receives the light emitted from the light source 102, and the detector 104 detects the gas subject to detection based on the variation in light intensity caused by the absorption of light by the gas subject to detection. The detector 104 according to this embodiment is exemplified by an infrared sensor configured to absorb infrared light and output an electrical signal. The infrared sensor is exemplified by a quantum type sensor such as a photodiode and a photoconductor configured to output a signal by photoelectric conversion, or a thermal type sensor such as a thermopile and a pyroelectric sensor configured to convert temperature variation due to infrared absorption into an electric signal. The detector 104 is mounted on a substrate 138 and is electrically connected to a wiring pattern (not shown) on the substrate 138.

The light source 102 and the detector 104 are provided such that a light emitting surface 102a of the light source 102 and a light receiving surface 104e of the detector 104 face each other. The gas introduction chamber 132 through which the gas subject to detection flows in is provided between the light source 102 and the detector 104. The gas introduction chamber 132 includes a first space 132a, a second space 132b, and a third space 132c. The first space 132a extends in a direction that intersects a direction in which the light source 102 and the detector 104 are arranged and is connected to the gas passage 130. The second space 132b extends from the first space 132a toward the light source 102. The third space 132c extends from the first space 132a toward the detector 104.

The tank gas in the constant-temperature tank 4 flows into the first space 132a via the gas passage 130. The tank gas passing through the first space 132a flows into the second space 132b and the third space 132c. By providing the second space 132b between the first space 132a and the light source 102 and providing the third space 132c between the first space 132a and the detector 104, the flow passage length of the tank gas from the constant-temperature tank 4 and the light source 102/detector 104 is extended. This lowers the temperature of the tank gas approaching the light source 102 and the detector 104 and inhibits an increase in the temperature of the light source 102 and the detector 104.

A certain distance (optical distance) needs to be provided between the light source 102 and the detector 104 for measurement of the gas subject to detection. In a structure where the first space 132a is connected to the light source 102 and the detector 104 without mediated by the second space 132b and the third space 132c, the width of the first space 132a needs to be extended to the optical distance. This might make it difficult to secure the strength of the member defining the gas introduction chamber 132. By providing the second space 132b and the third space 132c, on the other hand, the width of the first space 132a can be smaller than the optical distance. In this way, the strength of the member defining the gas introduction chamber 132 is secured more properly.

Preferably, the wall surface defining the second space 132b and the wall surface defining the third space 132c are coated with a metal film. The metal film may for example be made of a metal having a high reflectance in the infrared range such as gold, aluminum, chrome, etc. By providing a metal film, the light from the light source 102 is inhibited from being absorbed by the wall surface of the second space 132b and the third space 132c and the efficiency of guiding the light from the light source 102 to the detector 104 is increased. As a result, the sensitivity of detection by the gas sensor 100 is increased.

The light source 102 and the detector 104 are supported by a bracket 134. The bracket 134 includes a first housing 134a and a second housing 134b. The first housing 134a is provided adjacent to the second space 132b of the gas introduction chamber 132. The first housing 134a houses the light source 102. The light source 102 is provided such that the light emitting surface 102a faces the second space 132b.

The first housing 134a has an opening toward the second space 132b. The opening is blocked by a first lid member 140. Accordingly, the gas introduction chamber 132 and the first housing 134a are spaced apart from each other by the first lid member 140, and the tank gas is inhibited from leaking into the first housing 134a. This inhibits the accuracy of detection by the gas sensor 100 from being lowered. Preferably, the opening in the first housing 134a is hermetically sealed by the first lid member 140.

The second housing 134b is provided adjacent to the third space 132c of the gas introduction chamber 132. The second housing 134b houses the detector 104. The detector 104 is provided such that the light receiving surface 104e faces the third space 132c. The second housing 134b has an opening toward the third space 132c. The opening is blocked by a second lid member 142. Accordingly, the gas introduction chamber 132 and the second housing 134b are spaced apart from each other by the second lid member 142, and the tank gas is inhibited from leaking into the second housing 134b. This inhibits the accuracy of detection by the gas sensor 100 from being lowered. Preferably, the opening in the second housing 134b is hermetically sealed by the second lid member 142.

The first lid member 140 and the second lid member 142 are made of a material that transmits the light from the light source 102 (i.e., the ratio of absorption of emitted light is low). Therefore, the first lid member 140 and the second lid member 142 form an optical window. In this embodiment, infrared light is emitted from the light source 102. Therefore, the first lid member 140 and the second lid member 142 is made of, for example, germanium, silicon, sapphire, etc.

The light source 102, the first lid member 140, and the second lid member 142 are connected via the bracket 134 so as to be capable of conducting heat. This allows the heat of the light source 102 to heat the first lid member 140 and the second lid member 142. As a result, dew condensation on the first lid member 140 and the second lid member 142 is inhibited. By inhibiting dew condensation, the efficiency of light guidance from the light source 102 to the detector 104 is inhibited from being lowered. The bracket 134 is made of a material having a high thermal conductivity such as aluminum.

The detector 104 and the second lid member 142 are spaced apart from each other. By providing a space between the detector 104 and the second lid member 142, heat conduction from the second lid member 142 to the detector 104 is inhibited. This improves the accuracy of detection by the gas sensor 100. Meanwhile, the light source 102 and the first lid member 140 are provided to come into contact with each other. This allows the first lid member 140 to conduct the heat of the light source 102 efficiently. Further, the efficiency of light guidance from the light source 102 to the detector 104 is increased. The detector 104 is provided to be spaced apart from the wall surface of the second housing 134b. This inhibits the heat of the light source 102 from being conducted to the detector 104 via the bracket 134.

The light source 102 and the detector 104 communicate with a space outside the gas sensor 100, and, ultimately, the space outside the constant-temperature apparatus 1. More specifically, the first housing 134a also has an opening on the side opposite to the second space 132b. Similarly, the second housing 134b also has an opening on the side opposite to the third space 132c. For example, the first housing 134a and the second housing 134b are comprised of a through hole provided in the bracket 134. An opening (not shown) is provided in the casing 101a. This allows the light source 102 and the detector 104 to communicate with the space outside the gas sensor 100 and a space outside the constant-temperature apparatus 1. With such a configuration, air can be ventilated between the area where the light source 102 and the detector 104 are located and the space outside. The ventilation inhibits the accuracy of detection by the gas sensor 100 from being lowered due to the leakage of the tank gas from a gap between a packing 120, described later, and the through hole 4a or a gap between the packing 120 and the gas sensor 100.

The gas detection unit 101 may be provided with a heater (not shown) for heating the gas introduction chamber 132. By maintaining a constant temperature in the area of measurement of the gas subject to detection, i.e., in the space located between the light source 102 and the detector 104 where the gas subject to detection is located, the accuracy of detection by the gas sensor 100 is improved. Further, dew condensation on the first lid member 140 and the second lid member 142 is inhibited.

The gas passage 130 is a passage for the tank gas containing the gas subject to detection and is interposed between the constant-temperature tank 4 and the gas detection unit 101. By providing the gas passage 130, the gas detection unit 101 is spaced apart from the constant-temperature tank 4. This inhibits conduction of heat from an internal space of the constant-temperature tank 4 to the light source 102 and the detector 104. As a result, damage to the light source 102 and the detector 104 from the heat is inhibited so that the accuracy of detection by the gas sensor 100 is inhibited from being lowered.

The gas passage 130 is comprised of a tubular member and includes a first end 144, a second end 146 opposite to the first end 144, and a hollow part 148 extending from the first end 144 to the second end 146. The first end 144 is provided toward the gas detection unit 101. The second end 146 is provided toward the gas space where the gas subject to detection is located, i.e., toward the constant-temperature tank 4.

The end of hollow part 148 toward the first end 144 is connected to the first space 132a of the gas introduction chamber 132. The end of the hollow part 148 toward the second end 146 is connected to the internal space of the constant-temperature tank 4. A cap 150 is laid in the end of the hollow part 148 toward the second end 146. The cap 150 is made of a porous material having heat resistance and water repellency. For example, the cap 150 is made of a resin material like polytetrafluoroethylene (PTFE), a metal mesh, a punching metal, an expanded metal, etc. The heat resistance of the cap 150 is preferably 200° C. or higher. The cap 150 allows passage of the tank gas.

The tank gas containing the gas subject to detection is circulated between the constant-temperature tank and the gas detection unit 101 via the hollow part 148. The hollow part 148 has, at least in part, a shape in which the cross-sectional area N of the flow passage grows smaller away from the second end 146 and toward the first end 144 either in steps or continuously. In other words, the hollow part 148 is shaped such that the area of the cross section perpendicular to the direction in which the first end 144 and the second end 146 are arranged grows smaller away from the second end 146 and toward the first end 144 either in steps or continuously. The hollow part 148 shown in FIG. 1 is shaped such that the cross-sectional area N of the flow passage grows smaller continuously from the second end 146 toward the first end 144.

A large cross-sectional area N of the flow passage toward the second end 146 makes it easier to introduce the tank gas into the hollow part 148. Meanwhile, a small cross-sectional area N toward the first end 144 reduces the distance between the light source 102 and the detector 104. The distance between the light source 102 and the detector 104 in this embodiment is, for example, about 10 mm. By reducing the distance between the light source 102 and the detector 104, the light intensity of the light source 102 necessary for detection of the gas subject to detection is reduced. In other words, the gas subject to detection can be detected at a lower power. Another advantage is that the size of the gas detection unit 101 is prevented from growing.

The gas passage 130 is made of an adiabatic material at least in part. The gas passage 130 according to this embodiment is made of an adiabatic material in its entirety. Where only a part of the gas passage 130 is made of an adiabatic material, it is preferable to provide the adiabatic material such that the non-adiabatic material is discontinuous at some position between the first end 144 and the second end 146. By configuring at least a part of the gas passage 130 to be made of an adiabatic material, the heat in the internal space of the constant-temperature tank 4 is inhibited from being conducted to the light source 102 and the detector 104 via the gas passage 130.

For example, a material that causes the neighborhood of the light source 102 and the detector 104 to be at a temperature of 100° C. or lower when the temperature inside the constant-temperature tank 4 is 190° C. is selected. By selecting an adiabatic material having a high heat resistance, the adiabatic effect is enhanced. A high-temperature resistant resin is suitable as the adiabatic material. This is because a high-temperature resistant resin can be worked more easily and is more heat resistant than a metal. Specific examples of the adiabatic material include: polyphenylene sulfide (PPS); a fluororesin like polytetrafluoroethylene (PTFE) and Teflon (registered trademark); polyether ether ketone (PEEK); silicon resin; and polyamide-imide (PAI), etc.

In this embodiment, the gas passage 130 and the gas introduction chamber 132 of the gas detection unit 101 have an integrally molded structure made of an adiabatic material. In other words, the hollow part 148, the first space 132a, the second space 132b, and the third space 132c are defined inside a one-piece tubular member made of an adiabatic material.

The gas sensor 100 is fixed relative to the constant-temperature tank 4 by laying the packing 120 between the outer side surface of the gas passage 130 and the inner side surface of the through hole 4a while the gas passage 130 is being inserted into the through hole 4a of the constant-temperature tank 4. For example, the packing 120 is made of a silicon resin. The gas sensor 100 is configured such that the second end 146 of the gas passage 130 is exposed in the constant-temperature tank 4, the gas passage 130 is located in the through hole 4a, and the gas detection unit 101 is located outside the constant-temperature tank 4.

The gas sensor 100 is provided such that the gas passage 130 extends horizontally while the gas sensor 100 is being fixed relative to the constant-temperature tank 4. In other words, the gas sensor 100 is provided such that the first end 144 and the second end 146 are arranged in the horizontal direction. By placing the gas sensor 100 in the horizontal arrangement in this way, the dust or liquid is inhibited from entering the gas passage 130 or the gas introduction chamber 132, and the dust or liquid that has entered is inhibited from staying inside. This inhibits the accuracy of detection by the gas sensor 100 from being lowered.

The hollow part 148 and the first space 132a extend horizontally and in a direction normal to a wall surface 4b of the constant-temperature tank 4 while the gas sensor 100 is being fixed to the constant-temperature tank 4. The second space 132b and the third space 132c extend horizontally and parallel to the wall surface 4b of the constant-temperature tank 4. The light source 102 and the detector 104 are arranged in the horizontal direction. By providing the light source 102 and the detector 104 on the side surfaces of the gas sensor 100, the dust or moisture is inhibited from being collected on the light source 102 or the detector 104.

Further, the hollow part 148 has a portion substantially shaped in a truncated cone having a bottom surface located toward the second end 146 and a top surface located toward the first end 144. Therefore, the lower surface of the hollow part 148 in the perpendicular direction is tapered at least in part so as to incline downward in the perpendicular direction away from the first end 144 and toward the second end 146. This makes it easy for the dust or liquid to be discharged from inside the hollow part 148 or the gas introduction chamber 132 so that the dust or liquid is inhibited from being collected more successfully.

The tank gas in the constant-temperature tank 4 flows into the hollow part 148 via the cap 150. The tank gas flowing into the hollow part 148 advances toward the first end 144 and flows into the first space 132a of the gas introduction chamber 132. The tank gas flowing into the first space 132a flows into the second space 132b and the third space 132c. As a result, the first space 132a~ the third space 132c are filled with the tank gas.

The light of the light source 102 is emitted toward the gas subject to detection. In other words, the light of the light source 102 is emitted toward the second space 132b filled with the tank gas that contains the gas subject to detection. The light emitted from the light source 102 arrives at the detector 104 via the first lid member 140, the second space 132b, the area in the first space 132a sandwiched by the second space 132b and the third space 132c, the third space 132c, and the second lid member 142. In this process, the light of a certain wavelength is absorbed by the gas subject to detection located in the first space 132a~ the third space 132c. The detector 104 can detect the presence and density of the gas subject to detection based on the variation in the amount of light of the predetermined wavelength.

In this embodiment, the light source 102 emits infrared light, and the light of a wavelength 4.26 μm is absorbed by $CO_2$ located in the first space 132a~ the third space 132c. The detector 104 can detect the presence and density of $CO_2$ based on the intensity (amount of light) of the light of the wavelength 4.26 μm in the light received by the light receiving device, with reference to the intensity (amount of light) of the light of the wavelength 4.26 μm in the light emitted from the light source 102. For example, the density of $CO_2$ that the gas sensor 100 is capable of detecting is 0~20%.

We measured the density of $CO_2$ by using the gas sensor 100 according to this embodiment. The distance from the first end 144 to the second end 146 was configured to be 50 mm. The distance from the first end 144 to the center of the light emitting surface 102a in the direction in which the gas passage 130 and the gas detection unit 101 are arranged was configured to be 10 mm. The distance from the first lid member 140 to the second lid member 142 was configured to be 10 mm. The diameter of the hollow part 148 at the second end 146 was configured to be 20 mm. A $CO_2$ gas having the density of 5% was introduced into the gas introduction chamber 132. An infrared black-body radiation light source having a broad spectrum was used as the light source 102. An optical filter configured to transmit only the light of the wavelength 4.26 μm was provided on the light receiving surface 104e of the detector 104. The $CO_2$ density measurement revealed that the gas sensor 100 has an excellent detection sensitivity and is capable of detecting the density of $CO_2$ with a high accuracy. Further, the interior of the constant-temperature tank 4 was heated to 190° C., and the temperature around the light source 102 and the detector 104 was measured. We confirmed that the temperature around was 100° C. or lower.

As described above, the gas sensor 100 according to this embodiment is provided with the gas detection unit 101 including the light source 102 and the detector 104, and the gas passage 130 for circulating the gas subject to detection between the constant-temperature tank 4 and the gas detection unit 101. The gas passage 130 includes the first end 144, the second end 146, and the hollow part 148 that extends from the first end 144 to the second end 146. The hollow part 148 has a shape in which the cross-sectional area N of the flow passage grows smaller away from the second end 146 and toward the first end 144 either in steps or continuously. The first end 144 is provided toward the gas detection unit 101, and the second end 146 is provided toward the gas space. The gas subject to detection is circulated between the constant-temperature tank 4 and the gas detection unit 101 via the hollow part 148.

By providing the gas passage 130, the light source 102/the detector 104 and the constant-temperature tank 4 are thermally isolated. This inhibits damage to the light source 102 and the detector 104 due to the heat even when the temperature in the constant-temperature tank 4 becomes high such as when the temperature of the tank gas exceeds the withstand temperature of the light source 102 and the detector 104 or when the space filled with the tank gas is sterilized by dry sterilization. Accordingly, the accuracy of detection by the gas sensor 100 is inhibited from belong lowered.

By mounting the gas sensor 100 in the constant-temperature apparatus 1, the density of the gas subject to detection contained in the tank gas is detected with a high accuracy so that the performance of the constant-temperature apparatus 1 is improved. Since a dry sterilization process can be performed without removing the gas sensor 100, the ease of use of the constant-temperature apparatus 1 is improved.

In this embodiment, the light source 102 and the detector 104 are arranged in the horizontal direction, but the embodiment is not limited to this configuration. For example, the light source 102 and the detector 104 may be arranged in the perpendicular direction. In this case, it is preferable to provide the light source 102 below. This makes it easy for the heat of the light source 102 to be conducted to the first lid member 140 and the second lid member 142. As a result, dew condensation on the first lid member 140 is inhibited.

Embodiment 2

Figure 2:
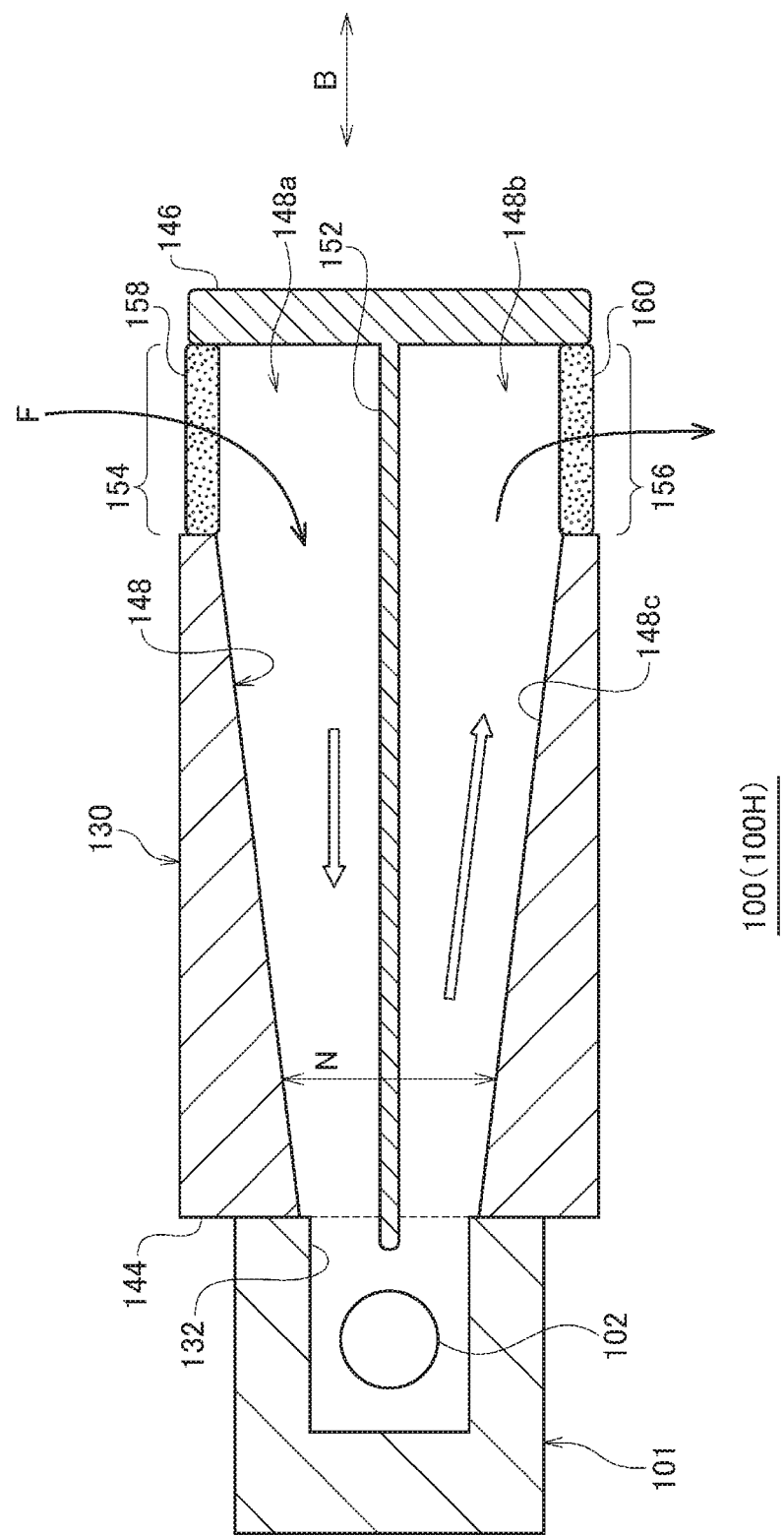
FIG. 2 is a perpendicular cross-sectional view schematically showing a gas sensor according to embodiment 2.
Figure 3A:
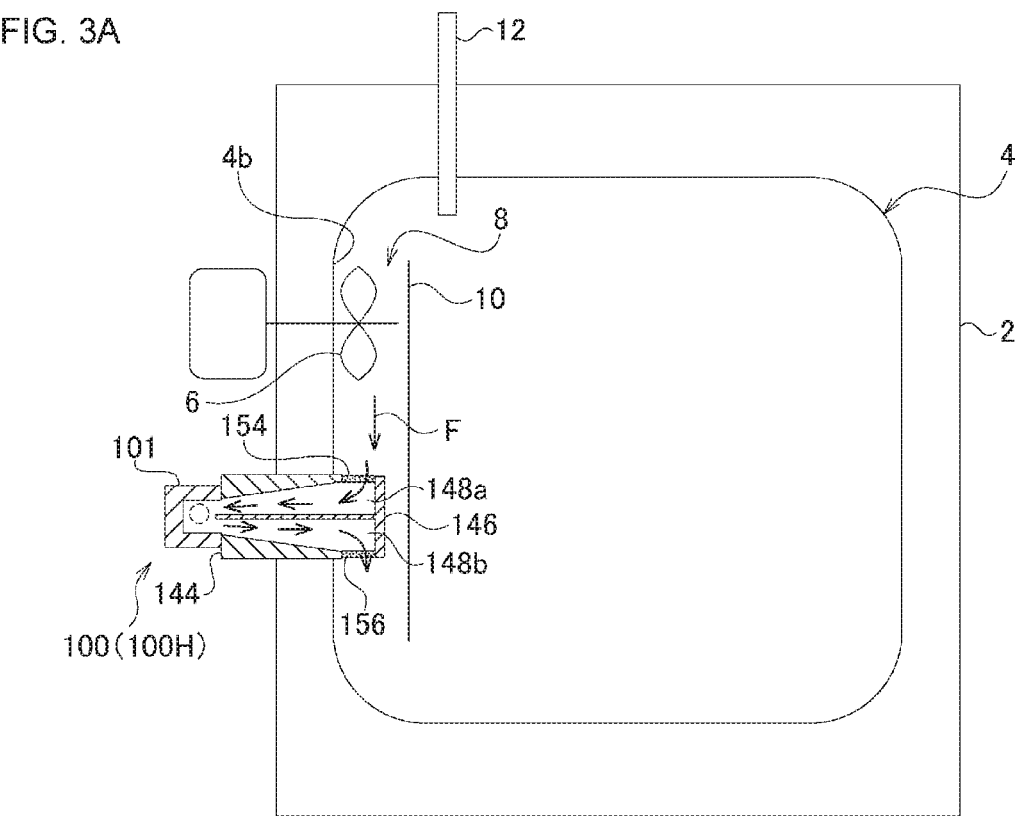
FIG. 3A is a perpendicular cross-sectional view schematically showing a constant-temperature apparatus according to embodiment 2.
Figure 3B:
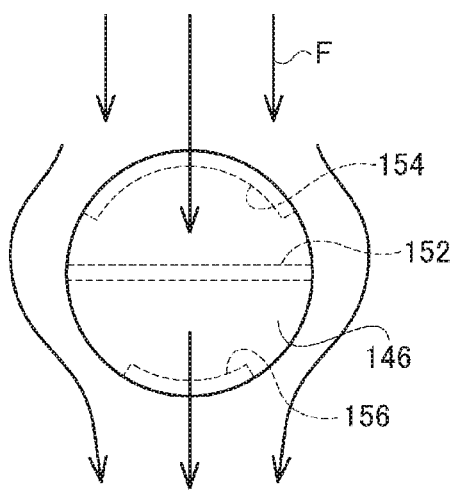
FIG. 3B schematically shows the flow of a tank gas.

FIG. 2 is a perpendicular cross-sectional view schematically showing a gas sensor according to embodiment 2. FIG. 3A is a perpendicular cross-sectional view schematically showing a constant-temperature apparatus according to embodiment 2. FIG. 3B schematically shows the flow of a tank gas. Those features of the gas sensor according to this embodiment that are different from those of embodiment 1 will mainly be described. Common features will be described briefly, or a description thereof will be omitted.

As shown in FIG. 2, the gas sensor 100 (100H) according to this embodiment is provided with the gas detection unit 101 including the light source 102, the detector 104 (see FIG. 1), and the gas introduction chamber 132, and with the gas passage 130. The gas passage 130 includes the first end 144, the second end 146, the hollow part 148, and a partition member 152. The first end 144 is provided toward the gas detection unit 101, and the second end 146 is provided toward the constant-temperature tank 4. The gas passage 130 circulates the gas subject to detection between the constant-temperature tank 4 and the gas detection unit 101 via the hollow part 148. The hollow part 148 has a shape in which the cross-sectional area N of the flow passage grows smaller away from the second end 146 and toward the first end 144. Further, a lower surface 148c of the hollow part 148 in the perpendicular direction is sloped so as to descend in the perpendicular direction away from the first end 144 and toward the second end 146.

The partition member 152 is a member that divides the hollow part 148 into at least two areas including a first area 148a and a second area 148b. In this embodiment, the partition member 152 divides the hollow part 148 into two areas, i.e., the first area 148a and the second area 148b. Each of the first area 148a and the second area 148b extends from the first end 144 side to the second end 146 side. In this embodiment, the partition member 152 extends from the first end 144 to the second end 146. Therefore, each of the first area 148a and the second area 148b extends from the first end 144 to the second end 146.

Further, the gas passage 130 includes a gas inflow port 154 and a gas outflow port 156. The gas inflow port 154 is provided at the second end 146 and connects the internal space of the constant-temperature tank 4 to the first area 148a. The gas outflow port 156 is provided at the second end 146 and connects the second area 148b to the internal space of the constant-temperature tank 4. The gas inflow port 154 is blocked by a porous member 158, and the gas outflow port 156 is blocked by a porous member 160. Materials for forming the porous members 158, 160 are exemplified by the materials to form the cap 150. The porous members 158, 160 allow passage of the gas subject to detection.

The aperture planes of gas inflow port 154 and the gas outflow port 156 extend parallel to a direction B (the direction indicated by an arrow B in FIG. 2) in which the first end 144 and the second end 146 are arranged. The fact that the porous member 158 and the porous member 160 extend parallel to the direction B also helps one to understand that the aperture planes of the gas inflow port 154 and the gas outflow port 156 extend parallel to the direction B. In other words, the gas inflow port 154 and the gas outflow port 156 are provided on the side surfaces of the gas passage 130.

As shown in FIG. 3A and FIG. 3B, the gas sensor 100 is provided on the wall surface 4b of the constant-temperature tank 4 such that the gas inflow port 154 and the gas outflow port 156 project from the wall surface 4b of the constant-temperature tank 4 into the internal space. Normally, a flow of the tank gas (the gas flow F) exits in the constant-temperature tank 4. The gas inflow port 154 is provided such that the aperture plane intersects the gas flow F in the constant-temperature tank 4, i.e., to intersect the direction of flow of the gas subject to detection. Preferably, the gas inflow port 154 is provided such that the aperture plane is perpendicular to the gas flow F. Further, the gas outflow port 156 is provided opposite to the gas inflow port 154 in the direction of the gas flow F.

Further, the gas inflow port 154 is provided upstream in the gas flow F, and the gas outflow port 156 is provided downstream of the gas inflow port 154 in the gas flow F. Further, the second end 146 is provided in an area where the gas subject to detection flows downward in the perpendicular direction in the constant-temperature tank 4. Further, the gas inflow port 154 is provided above the gas outflow port 156 in the perpendicular direction.

The tank gas located in the constant-temperature tank 4 and containing the gas subject to detection flows into the hollow part 148 from the gas inflow port 154, flows in the first area 148a toward the first end 144, and arrives at the gas detection unit 101. In association with this, the tank gas located in the gas detection unit 101 and containing the gas subject to detection flows in the second area 148b toward the second end 146 and flows out from the gas outflow port 156 into the constant-temperature tank 4.

Thus, by using the partition member 152 to divide the hollow part 148 into the first area 148a and the second area 148b, providing the gas inflow port 154 in the first area 148a, and providing the gas outflow port 156 in the second area 148b, the flow of the tank gas in the hollow part 148 is straightened to create a convection flow. The feature makes it possible to introduce the gas subject to detection into the gas detection unit 101 more efficiently and, accordingly, to replace the gas in the gas introduction chamber 132 promptly. Accordingly, the speed of detection by the gas sensor 100 is improved.

By projecting the second end 146 of the gas sensor 100 into the area where the gas flow F is located, the pressure applied on the surface upstream in the gas flow F, i.e., the pressure applied to the surface directly facing the gas flow F, will be higher than the pressure applied to the downstream surface, i.e., the pressure applied to the surface reached by the gas flow F in a roundabout fashion. Therefore, a pressure difference is created between the upstream surface and the downstream surface. Thus, by providing the gas inflow port 154 on the upstream side in the gas flow F and providing the gas outflow port 156 on the downstream side, the pressure difference is utilized to introduce the tank gas into the hollow part 148 smoothly.

Further, the gas inflow port 154 has an aperture plane that extends parallel to the direction B in which the first end 144 and the second end 146 are arranged, and the aperture plane is provided to intersect the direction of the gas flow F. This allows the gas flow F to hit the gas inflow port 154 directly so that the efficiency of introducing the gas subject to detection into the gas detection unit 101 is further increased.

In further accordance with this embodiment, the second end 146 is provided in an area where the tank gas flows downward in the perpendicular direction, and the gas inflow port 154 is provided above the gas outflow port 156 in the perpendicular direction. This further increases the aforementioned pressure difference by utilizing the gravity exerted on the tank gas. Accordingly, the efficiency of introducing the gas subject to detection into the gas detection unit 101 is further increased.

Further, the aperture area of the gas inflow port 154 is larger than that of the gas outflow port 156. This creates a differential pressure in the first area 148a and the second area 148b due to the difference in aperture area (Bernoulli's principle). To be more specific, the pressure in the second area 148b will be lower than in the first area 148a. Therefore, the flow rate of the tank gas in the second area 148b will be higher than in the first area 148a. Accordingly, the efficiency of introducing the gas subject to detection into the gas detection unit 101 is further increased.

Further, the constant-temperature apparatus 1 according to this embodiment is further provided with a fan 6 that blows air to cause the tank gas to flow along the wall surface 4b. The gas sensor 100 is provided downstream of the fan 6 in the gas flow F. By providing the fan 6, the pressure difference between the gas inflow port 154 side and the gas outflow port 156 side is further increased. Accordingly, the efficiency of introducing the gas subject to detection into the gas detection unit 101 is further increased.

The constant-temperature apparatus 1 is further provided with a gas passage 8 in which the tank gas flows. The gas passage 8 is provided along the wall surface 4b in the interior space of the constant-temperature tank 4. For example, the gas passage 8 is comprised of a partition plate 10 extending along the wall surface 4b and the wall surface 4b. By providing the gas passage 8, it is further ensured that the gas flow F hits the second end 146 of the gas sensor 100. Accordingly, the efficiency of introducing the gas subject to detection into the gas detection unit 101 is further increased. In this embodiment, the fan 6 is provided near the entrance of the gas passage 8. Further, the constant-temperature apparatus 1 includes a gas introduction pipe 12 for introducing the tank gas into the constant-temperature tank 4. Preferably, the gas introduction pipe 12 is provided such that the fan 6 is positioned between the gas introduction pipe 12 and the gas sensor 100.

The following variations are possible for the gas sensor 100 according to embodiment 2. FIG. 4A is a perpendicular cross-sectional view schematically showing a gas sensor according to variation 1. FIG. 4B is a perpendicular cross-sectional view schematically showing a gas sensor according to variation 2.

As shown in FIG. 4A, the aperture planes of the gas inflow port 154 and the gas outflow port 156 of the gas sensor 100 (100H') according to variation 1 extend in a direction intersecting the direction B in which the first end 144 and the second end 146 are arranged. Therefore, the aperture planes of the gas inflow port 154 and the gas outflow port 156 extend substantially parallel to the gas flow F in the constant-temperature tank 4. The gas inflow port 154 and the gas outflow port 156 are blocked by a porous member 162 that allows passage of the gas subject to detection. Materials for forming the porous member 162 are exemplified by the materials to form the cap 150. The configuration also allows the tank gas to be introduced into the hollow part 148 by utilizing the pressure difference between the gas inflow port 154 side and the gas outflow port 156 side.

As shown in FIG. 4B, the gas sensor 100 (100H") according to variation 2 has a structure in which embodiment 2 and variation 1 are combined. In other words, the aperture planes of the gas inflow port 154 and the gas outflow port 156 have an area in which they extend parallel to the direction B in which the first end 144 and the second end 146 are arranged and an area in which they extend in a direction intersecting the direction B in which the first end 144 and the second end 146 are arranged. This increases the amount of tank gas introduced into the hollow part 148 so that the efficiency of introducing the gas subject to detection into the gas detection unit 101 is further increased.

Embodiment 3

Figure 5A:
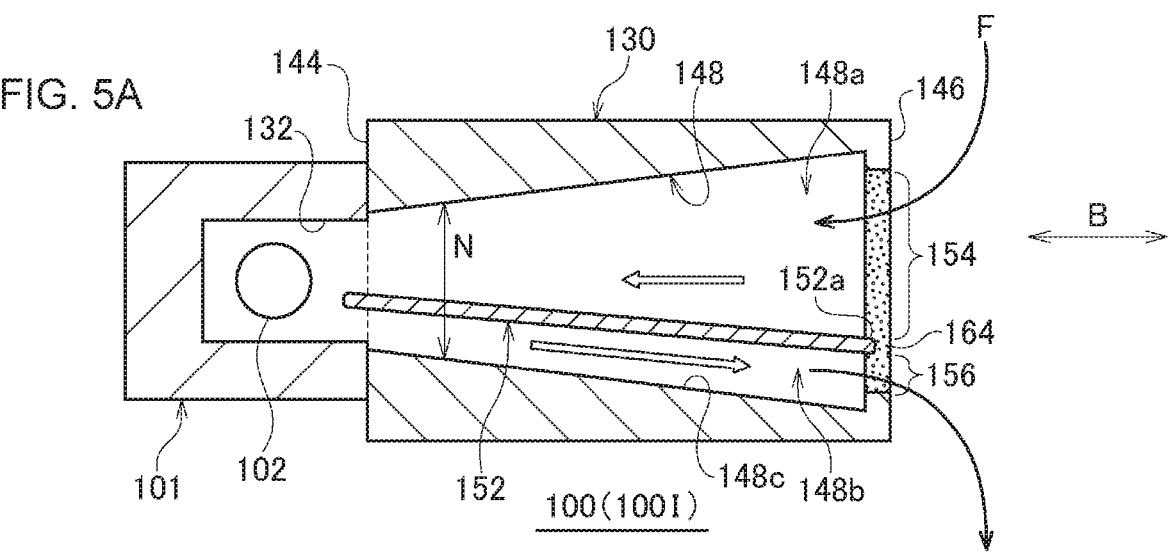
FIG. 5A is a perpendicular cross-sectional view schematically showing a gas sensor according to embodiment 3.
Figure 5B:
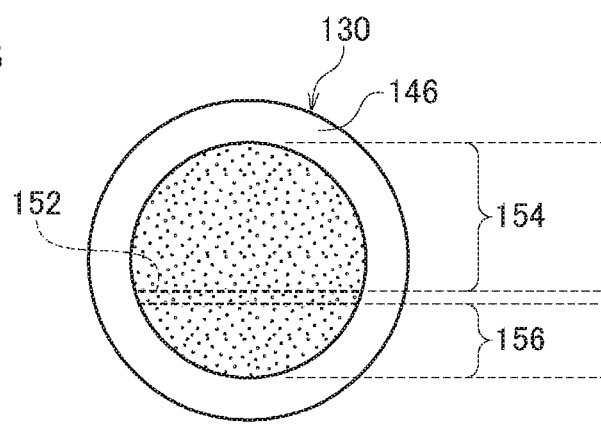
FIG. 5B schematically shows the end face of the gas sensor according to embodiment 3 at the second end.

FIG. 5A is a perpendicular cross-sectional view schematically showing a gas sensor according to embodiment 3. FIG. 5B schematically shows the end face of the gas sensor according to embodiment 3 at the second end. Those features of the gas sensor according to this embodiment that are different from those of embodiment 1 will mainly be described. Common features will be described briefly, or a description thereof will be omitted.

The gas sensor 100 (100I) according to this embodiment is provided with the gas detection unit 101 including the light source 102, the detector 104 (see FIG. 1), and the gas introduction chamber 132, and with the gas passage 130. The gas passage 130 includes the first end 144, the second end 146, the hollow part 148, and the partition member 152. The first end 144 is provided toward the gas detection unit 101, and the second end 146 is provided toward the constant-temperature tank 4. The gas passage 130 circulates the gas subject to detection between the constant-temperature tank 4 and the gas detection unit 101 via the hollow part 148. The hollow part 148 has a shape in which the cross-sectional area N of the flow passage grows smaller away from the second end 146 and toward the first end 144. Further, a lower surface 148c of the hollow part 148 in the perpendicular direction is sloped so as to descend in the perpendicular direction away from the first end 144 and toward the second end 146.

The partition member 152 is a member that divides the hollow part 148 into at least two areas including a first area 148a and a second area 148b. In this embodiment, the partition member 152 divides the hollow part 148 into two areas, i.e., the first area 148a and the second area 148b. Each of the first area 148a and the second area 148b extends from the first end 144 to the second end 146.

Further, the gas passage 130 includes a gas inflow port 154 and a gas outflow port 156. The gas inflow port 154 is provided at the second end 146 and connects the internal space of the constant-temperature tank 4 to the first area 148a. The gas outflow port 156 is provided at the second end 146 and connects the second area 148b to the internal space of the constant-temperature tank 4. The gas inflow port 154 and the gas outflow port 156 are blocked by a porous member 164 that allows passage of the gas subject to detection. Materials for forming the porous member 164 are exemplified by the materials to form the cap 150. The aperture planes of the gas inflow port 154 and the gas outflow port 156 extend in a direction intersecting the direction B in which the first end 144 and the second end 146 are arranged.

Further, the aperture area of the gas inflow port 154 is larger than that of the gas outflow port 156. In this embodiment, an end 152a of the partition member 152 toward the second end 146 is embedded in the porous member 164. The end 152a forms a boundary between the gas inflow port 154 and the gas outflow port 156. Further, the partition member 152 is sloped so as to descend in the perpendicular direction away from the first end 144 and toward the second end 146. This results in the formation of the gas inflow port 154 that has a larger aperture area and the gas outflow port 156 that has a smaller aperture area.

The gas sensor 100 is provided on the wall surface 4b of the constant-temperature tank 4 (see FIGS. 1 and 3(A)). Normally, a flow of tank gas (the gas flow F) exits in the constant-temperature tank 4. The gas inflow port 154 is provided upstream in the gas flow F, and the gas outflow port 156 is provided downstream of the gas inflow port 154 in the gas flow F. Further, the second end 146 is provided in an area where the gas subject to detection flows downward in the perpendicular direction in the constant-temperature tank 4. Further, the gas inflow port 154 is provided above the gas outflow port 156 in the perpendicular direction.

The tank gas located in the constant-temperature tank 4 and containing the gas subject to detection flows into the hollow part 148 from the gas inflow port 154, flows in the first area 148a toward the first end 144, and arrives at the gas detection unit 101. In association with this, the tank gas located in the gas detection unit 101 and containing the gas subject to detection flows in the second area 148b toward the second end 146 and flows out from the gas outflow port 156 into the constant-temperature tank 4.

Thus, by using the partition member 152 to divide the hollow part 148 into the first area 148a and the second area 148b, providing the gas inflow port 154 in the first area 148a, and providing the gas outflow port 156 in the second area 148b, the flow of the tank gas in the hollow part 148 is straightened. Accordingly, the speed of detection by the gas sensor 100 is improved.

Further, the aperture area of the gas inflow port 154 is larger than that of the gas outflow port 156. This creates a differential pressure in the first area 148a and the second area 148b due to the difference in aperture area. To be more specific, the pressure in the second area 148b will be lower than in the first area 148a. Therefore, the flow rate of the tank gas in the second area 148b will be higher than in the first area 148a. Accordingly, the efficiency of introducing the gas subject to detection into the gas detection unit 101 is further increased.

The slope of the partition member 152 causes the cross-sectional area of the flow passage in the second area 148b to be smaller than the cross-sectional area of the flow passage in the first area 148a at least in part. This causes the flow rate of the tank gas in the second area 148b to be higher than that in the first area 148a. Accordingly, the efficiency of introducing the gas subject to detection into the gas detection unit 101 is further increased.

In further accordance with this embodiment, the second end 146 is provided in an area where the tank gas flows downward in the perpendicular direction, and the gas inflow port 154 is provided above the gas outflow port 156 in the perpendicular direction. The feature further increases the pressure difference between the gas inflow port 154 and the gas outflow port 156 by utilizing the gravity exerted on the tank gas. Accordingly, the efficiency of introducing the gas subject to detection into the gas detection unit 101 is further increased.

Figure 6A:
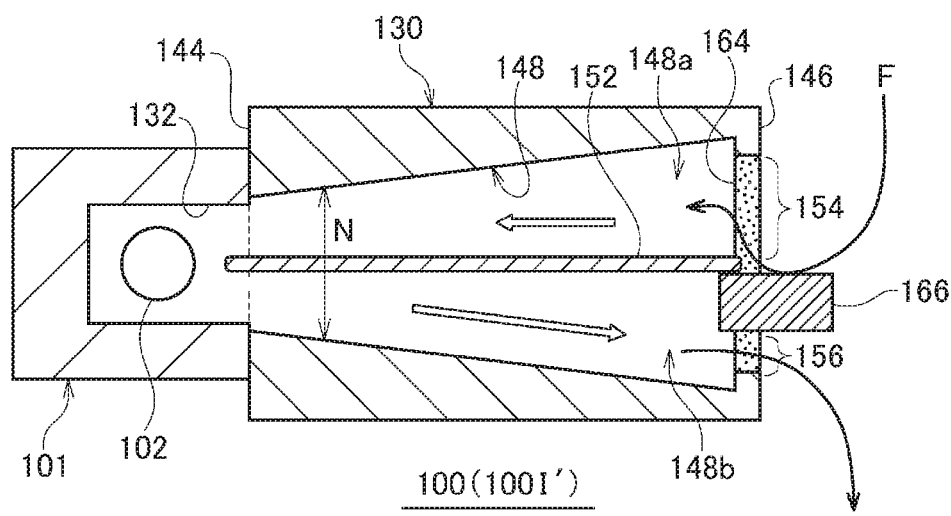
FIG. 6A is a perpendicular cross-sectional view schematically showing a gas sensor according to variation 3.
Figure 6B:
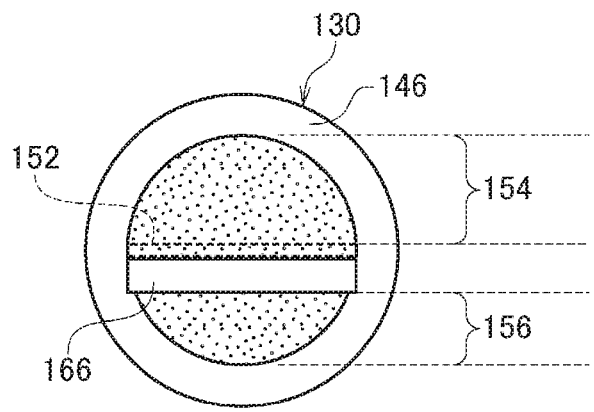
FIG. 6B schematically shows the end face of the gas sensor according to variation 3 at the second end.

The following variations are possible for the gas sensor 100 according to embodiment 3. FIG. 6A is a perpendicular cross-sectional view schematically showing a gas sensor according to variation 3. FIG. 6B schematically shows the end face of the gas sensor according to variation 3 at the second end.

As shown in FIGS. 6A and 6B, a difference in the aperture area is provided between the gas inflow port 154 and the gas outflow port 156 by blocking a portion of the gas outflow port 156 in the gas sensor 100 (100I') according to variation 3. In this variation, a straightener 166 having a fin structure is used as a member to block a portion of the gas outflow port 156.

The straightener 166 is a member that projects from an area at the second end 146 between the gas inflow port 154 and the gas outflow port 156 into the interior space of the constant-temperature tank 4. The end of the straightener 166 toward the gas passage 130 is embedded in an area of the porous member 164 in contact with the second area 148b. This causes the aperture area of the gas outflow port 156 to be smaller than the aperture area of the gas inflow port 154.

The part of the straightener 166 projecting into the interior space of the constant-temperature tank 4 restricts the gas flow F (the flow of the gas subject to detection) in the constant-temperature tank 4. A portion of the tank gas flowing in the constant-temperature tank 4 hits the straightener 166 as it passes the neighborhood of the second end 146 and is guided to travel toward the gas inflow port 154.

Therefore, the straightener 166 can guide the tank gas into the hollow part 148. This further increases the efficiency of introducing the gas subject to detection into the gas detection unit 101.

Embodiment 4

Figure 7:
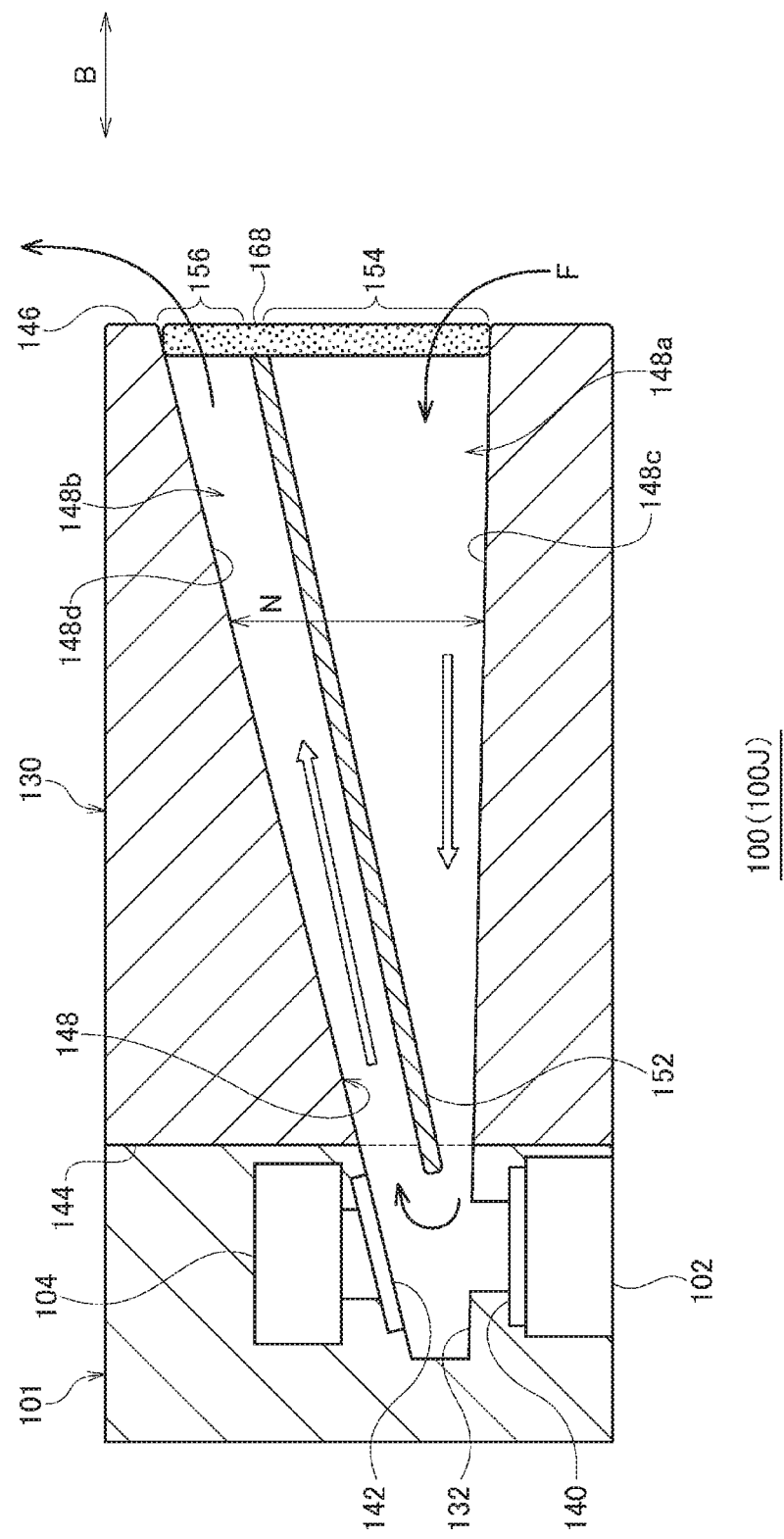
FIG. 7 is a perpendicular cross-sectional view schematically showing a gas sensor according to embodiment 4.

FIG. 7 is a perpendicular cross-sectional view schematically showing a gas sensor according to embodiment 4. Those features of the gas sensor according to this embodiment that are different from those of embodiment 1 will mainly be described. Common features will be described briefly, or a description thereof will be omitted.

The gas sensor 100 (100J) according to this embodiment is provided with the gas detection unit 101 including the light source 102, the detector 104, and the gas introduction chamber 132, and with the gas passage 130. The gas passage 130 includes the first end 144, the second end 146, the hollow part 148, and the partition member 152. The first end 144 is provided toward the gas detection unit 101, and the second end 146 is provided toward the constant-temperature tank 4. The gas passage 130 circulates the gas subject to detection between the constant-temperature tank 4 and the gas detection unit 101 via the hollow part 148. The hollow part 148 has a shape in which the cross-sectional area N of the flow passage grows smaller away from the second end 146 and toward the first end 144. Further, a lower surface 148c of the hollow part 148 in the perpendicular direction is sloped so as to descend in the perpendicular direction away from the first end 144 and toward the second end 146.

The partition member 152 is a member that divides the hollow part 148 into at least two areas including a first area 148a and a second area 148b. In this embodiment, the partition member 152 divides the hollow part 148 into two areas, i.e., the first area 148a and the second area 148b. Each of the first area 148a and the second area 148b extends from the first end 144 to the second end 146.

Further, the gas passage 130 includes a gas inflow port 154 and a gas outflow port 156. The gas inflow port 154 is provided at the second end 146 and connects the internal space of the constant-temperature tank 4 to the first area 148a. The gas outflow port 156 is provided at the second end 146 and connects the second area 148b to the internal space of the constant-temperature tank 4. The gas inflow port 154 and the gas outflow port 156 are blocked by a porous member 168 that allows passage of the gas subject to detection. Materials for forming the porous member 168 are exemplified by the materials to form the cap 150. The aperture planes of the gas inflow port 154 and the gas outflow port 156 extend in a direction intersecting the direction B in which the first end 144 and the second end 146 are arranged. Further, the aperture area of the gas inflow port 154 is larger than that of the gas outflow port 156.

In this embodiment, the light source 102 is provided below the detector 104 in the perpendicular direction. Further, the gas inflow port 154 is provided below the gas outflow port 156 in the perpendicular direction. Therefore, the first area 148a extends below the second area 148b in the perpendicular direction. In the gas detection unit 101, the heat of the light source 102 provided below in the perpendicular direction heats the gas in the gas introduction chamber 132. This creates a flow of gas that rises from the light source 102 toward the detector 104. The gas turned into an upward flow in the gas introduction chamber 132 advances in the second area 148b toward the second end 146 and flows out from the gas outflow port 156. Meanwhile, the pressure is lowered in the first area 148a due to the upward flow of the gas caused by the heat of the light source 102. This causes the tank gas to flow into the first area 148*a* from the gas inflow port 154. This creates a tank gas circulation, in which the tank gas flowing into the hollow part 148 from the gas inflow port 154 arrives at the gas detection unit 101 and flows out from the gas outflow port 156 by flowing through the hollow part 148 again.

Thus, by using the partition member 152 to divide the hollow part 148 into the first area 148*a* and the second area 148*b*, providing the gas inflow port 154 in the first area 148*a*, and providing the gas outflow port 156 in the second area 148*b*, the flow of the tank gas in the hollow part 148 is straightened. Accordingly, the speed of detection by the gas sensor 100 is improved. Since the gas subject to detection is circulated by using the heat of the light source 102, the speed of detection by the gas sensor 100 is further improved.

The hollow part 148 is tapered such that an upper surface 148*d* in the perpendicular direction inclines upward in the perpendicular direction away from the first end 144 and toward the second end 146. This makes the flow of the tank gas from the gas detection unit 101 to the gas outflow port 156 smoother. Accordingly, the speed of detection by the gas sensor 100 is improved. The slope of the upper surface 148*d* in the perpendicular direction is steeper than the slope of the lower surface 148*c* in the perpendicular direction. Accordingly, the size of the gas sensor 100 is prevented from growing.

The aperture area of the gas inflow port 154 is larger than that of the gas outflow port 156. This creates a differential pressure in the first area 148*a* and the second area 148*b* due to the difference in aperture area. Therefore, the flow rate of the tank gas in the second area 148*b* will be higher than in the first area 148*a*. Accordingly, the efficiency of introducing the gas subject to detection into the gas detection unit 101 is further increased. Further, the partition member 152 is tapered so as to ascend in the perpendicular direction away from the first end 144 and toward the second end 146. This causes the cross-sectional area of the flow passage in the second area 148*b* to be smaller than the cross-sectional area of the flow passage in the first area 148*a* at least in part. Therefore, the flow rate of the tank gas in the second area 148*b* will be higher than in the first area 148*a*. Accordingly, the efficiency of introducing the gas subject to detection into the gas detection unit 101 is further increased.

Embodiment 5

FIG. 8A is a perpendicular cross-sectional view schematically showing a gas sensor according to embodiment 5. FIG. 8B is a horizontal cross-sectional view schematically showing the gas sensor according to embodiment 5. Those features of the gas sensor according to this embodiment that are different from those of embodiments 1 and 2 will mainly be described. Those features that are common to embodiments 1 and 2 will be described briefly, or a description thereof will be omitted.

The gas sensor 100 (100K) according to this embodiment is provided with the gas detection unit 101 including the light source 102 and the detector 104, and with the gas passage 130. The gas passage 130 includes the first end 144, the second end 146, the hollow part 148, and the partition member 152. The first end 144 is provided toward the gas detection unit 101, and the second end 146 is provided toward the constant-temperature tank 4. The gas passage 130 circulates the gas subject to detection between the constant-temperature tank 4 and the gas detection unit 101 via the hollow part 148. The hollow part 148 has a shape in which the cross-sectional area N of the flow passage grows smaller away from the second end 146 and toward the first end 144. Further, a lower surface 148*c* of the hollow part 148 in the perpendicular direction is sloped so as to descend in the perpendicular direction away from the first end 144 and toward the second end 146.

The partition member 152 is a member that divides the hollow part 148 into at least two areas including a first area 148*a* and a second area 148*b*. In this embodiment, the partition member 152 divides the hollow part 148 into two areas, i.e., the first area 148*a* and the second area 148*b*. Each of the first area 148*a* and the second area 148*b* extends from the first end 144 side to the second end 146 side. The ends of the partition member 152 do not reach the first end 144 and the second end 146. Therefore, the first area 148*a* and the second area 148*b* communicate with each other in the hollow part 148. The area of connection between the first area 148*a* and the second area 148*b* at the first end 144 side and the area of connection at the second end 146 side are configured such that a majority or the entirety of the tank gas flowing from the gas inflow port 154 flows toward the first end 144 via the first area 148*a*.

Further, the gas passage 130 includes a gas inflow port 154 and a gas outflow port 156. The gas inflow port 154 is provided at the second end 146 and connects the constant-temperature tank 4 to the first area 148*a*. The gas outflow port 156 is provided at the second end 146 and connects the second area 148*b* to the constant-temperature tank 4. The gas inflow port 154 is blocked by a porous member 158, and the gas outflow port 156 is blocked by a porous member 160. The aperture planes of the gas inflow port 154 and the gas outflow port 156 extend parallel to a direction B in which the first end 144 and the second end 146 are arranged. In other words, the gas inflow port 154 and the gas outflow port 156 are provided on the side surfaces of the gas passage 130.

The light source 102 is provided such that the light emitting surface 102*a* faces the hollow part 148. In other words, the light source 102 is provided such that the emitted light M passes through the hollow part 148. The detector 104 is provided such that the light receiving surface 104*e* faces the hollow part 148. The relative positions of the light source 102 and the detector 104 are defined such that the light M emitted from the light source 102 does not directly irradiate the light receiving surface 104*e* of the detector 104.

Further, the gas sensor 100 is provided with a light reflecting part 108. The light reflecting part 108 is fixed to the second end 146 of the gas passage 130. The light reflecting part 108 includes a concave reflecting surface 108*a*. The concave reflecting surface 108*a* is provided to face the hollow part 148. This causes the concave reflecting surface 108*a* to be opposite to the light source 102 and the detector 104. The concave reflecting surface 108*a* is formed by, for example, forming a film of metal such as gold, aluminum, and chromium having a high reflectance in the infrared region on the surface of the light reflecting part 108.

The light M emitted from the light source 102 travels in the hollow part 148, is reflected by the concave reflecting surface 108*a*, travels in the hollow part 148 again, and arrives at the detector 104. Therefore, the hollow part 148 also functions as a passage of the light M. A metal film 114 is formed on the wall surface defining the hollow part 148. The metal film 114 is made of, for example, gold, aluminum, chromium, etc. having a high reflectance in the infrared region. By providing the metal film 114, the light of the light source 102 is inhibited from being absorbed by the wall surface of the hollow part 148, and the efficiency of light guidance from the light source 102 to the detector 104 is increased. As a result, the sensitivity of detection by the gas sensor 100 is increased. Further, the partition member 152 is made of a metal. For example, the partition member 152 is made of gold, aluminum, chromium, etc. having a high reflectance in the infrared region. Further, the surface of the partition member 152 is preferably mirror-finished to increase the reflectance for the light M. This increases the efficiency of light guidance from the light source 102 to the detector 104.

The gas detection unit 101 includes a bracket 170. The bracket 170 includes a housing 172 for the light source 102 and the detector 104. The housing 172 includes an opening toward the hollow part 148. The opening is blocked by a lid member 174. Preferably, the opening in the housing 172 is hermetically sealed by the lid member 174. The lid member 174 is made of a material that transmits the light from the light source 102. In this embodiment, infrared light is emitted from the light source 102. Therefore, the lid member 174 is made of, for example, germanium, silicon, sapphire, etc.

The gas sensor 100 is provided on the wall surface 4b of the constant-temperature tank 4 such that the gas inflow port 154 and the gas outflow port 156 project from the wall surface 4b of the constant-temperature tank 4 into the tank (see FIG. 3A). The gas inflow port 154 is provided such that the aperture plane intersects the gas flow F in the constant-temperature tank 4 (i.e., the direction of flow of the gas subject to detection). Preferably, the gas inflow port 154 is provided such that the aperture plane is perpendicular to the gas flow F. Further, the gas outflow port 156 is provided opposite to the gas inflow port 154 in the direction of the gas flow F.

Further, the gas inflow port 154 is provided upstream in the gas flow F, and the gas outflow port 156 is provided downstream of the gas inflow port 154 in the gas flow F. Further, the second end 146 is provided in an area where the gas subject to detection flows downward in the perpendicular direction in the constant-temperature tank 4. Further, the gas inflow port 154 is provided above the gas outflow port 156 in the perpendicular direction.

The tank gas located in the constant-temperature tank 4 flows into the hollow part 148 from the gas inflow port 154, flows in the first area 148a toward the first end 144, and arrives at the gas detection unit 101. In association with this, the tank gas located in the gas detection unit 101 (the tank gas in contact with the lid member 174) flows in the second area 148b toward the second end 146 and flows out from the gas outflow port 156 into the constant-temperature tank 4.

Thus, by using the partition member 152 to divide the hollow part 148 into the first area 148a and the second area 148b, providing the gas inflow port 154 in the first area 148a, and providing the gas outflow port 156 in the second area 148b, the flow of the tank gas in the hollow part 148 is straightened. This further increases the efficiency of introducing the gas subject to detection into the gas detection unit 101 and improves the speed of detection by the gas sensor 100.

By projecting the second end 146 of the gas sensor 100 into the area where the gas flow F is located, a pressure difference between the surface upstream in the gas flow F and the surface downstream is created. By providing the gas inflow port 154 on the upstream side in the gas flow F and providing the gas outflow port 156 on the downstream side, the pressure difference is utilized to introduce the tank gas into the hollow part 148 smoothly.

Further, the gas inflow port 154 has an aperture plane that extends parallel to the direction B in which the first end 144 and the second end 146 are arranged, and the aperture plane is provided to intersect the direction of the gas flow F. This further increases the efficiency of introducing the gas subject to detection into the gas detection unit 101. In further accordance with this embodiment, the second end 146 is provided in an area where the tank gas flows downward in the perpendicular direction, and the gas inflow port 154 is provided above the gas outflow port 156 in the perpendicular direction. This further increases the efficiency of introducing the gas subject to detection into the gas detection unit 101.

The aperture area of the gas inflow port 154 is larger than that of the gas outflow port 156. This creates a differential pressure in the first area 148a and the second area 148b due to the difference in aperture area. This further increases the efficiency of introducing the gas subject to detection into the gas detection unit 101.

The light M emitted from the light source 102 travels in the hollow part 148 and arrives at a second end 106b either directly or by being reflected by the metal film 114 and the partition member 152. The light M is reflected by the concave reflecting surface 108a, travels again in the hollow part 148, and arrives at the detector 104 either directly or by being reflected by the metal film 114 and the partition member 152. In this process, the light M passes through the tank gas filling the hollow part 148. During the passage, the light of a predetermined wavelength is absorbed by the gas subject to detection contained in the tank gas. The detector 104 is capable of detecting the presence and density of the gas subject to detection based on the intensity (amount of light) of the light of the predetermined wavelength in the light received by the light receiving device, with reference to the intensity (amount of light) of the light of the predetermined wavelength in the light emitted from the light source 102.

By causing the light M to pass through the hollow part 148 filled with the tank gas to detect the gas subject to detection, the measurement distance of the gas subject to detection is increased. As a result, the gas that requires a relatively long measurement distance such as water vapor ($H_2O$) is detected with a higher accuracy. Even if the gas subject to detection is in a very small amount, the gas is detected with a high accuracy.

Preferably, the opening in the hollow part 148 at the first end 144 is elliptical, and the opening at the second end 146 is circular. The hollow part 148 has a shape that changes progressively from elliptical to circular from the first end 144 to the second end 146. This improves the efficiency of transmission of the light M from the light source 102 to the detector 104 as compared with a hollow part that is circular or elliptical at both ends.

Where the first end 144 of the hollow part 148 is configured to be elliptical, it is preferable that the light source 102 and the detector 104 are arranged at positions point-symmetric with respect to the center of the ellipse (the point of intersection of the long axis and the short axis of the ellipse) when viewed in the direction in which the light source 102/the detector 104, and the hollow part 148 are arranged. In this case, arbitrary parts of the light source 102 and the detector 104 are provided at point-symmetric positions by way of example. Alternatively, the center of the light emitting surface 102a of the light source 102 and the center of a second detection unit 104b of the detector 104 are provided at point-symmetric positions. The feature allows the light emitted from the light source 102 to be focused on the detector 104 more properly. The feature improves the efficiency of transmitting the light M. Further, the light source 102 and the detector 104 are more preferably provided on the long diameter of the ellipse. Still more preferably, the light source 102 is provided on one focal point of the ellipse, and the detector 104 is provided on the other focal point of the ellipse. The feature further improves the efficiency of transmitting the light M.

Embodiment 6

Figure 9:
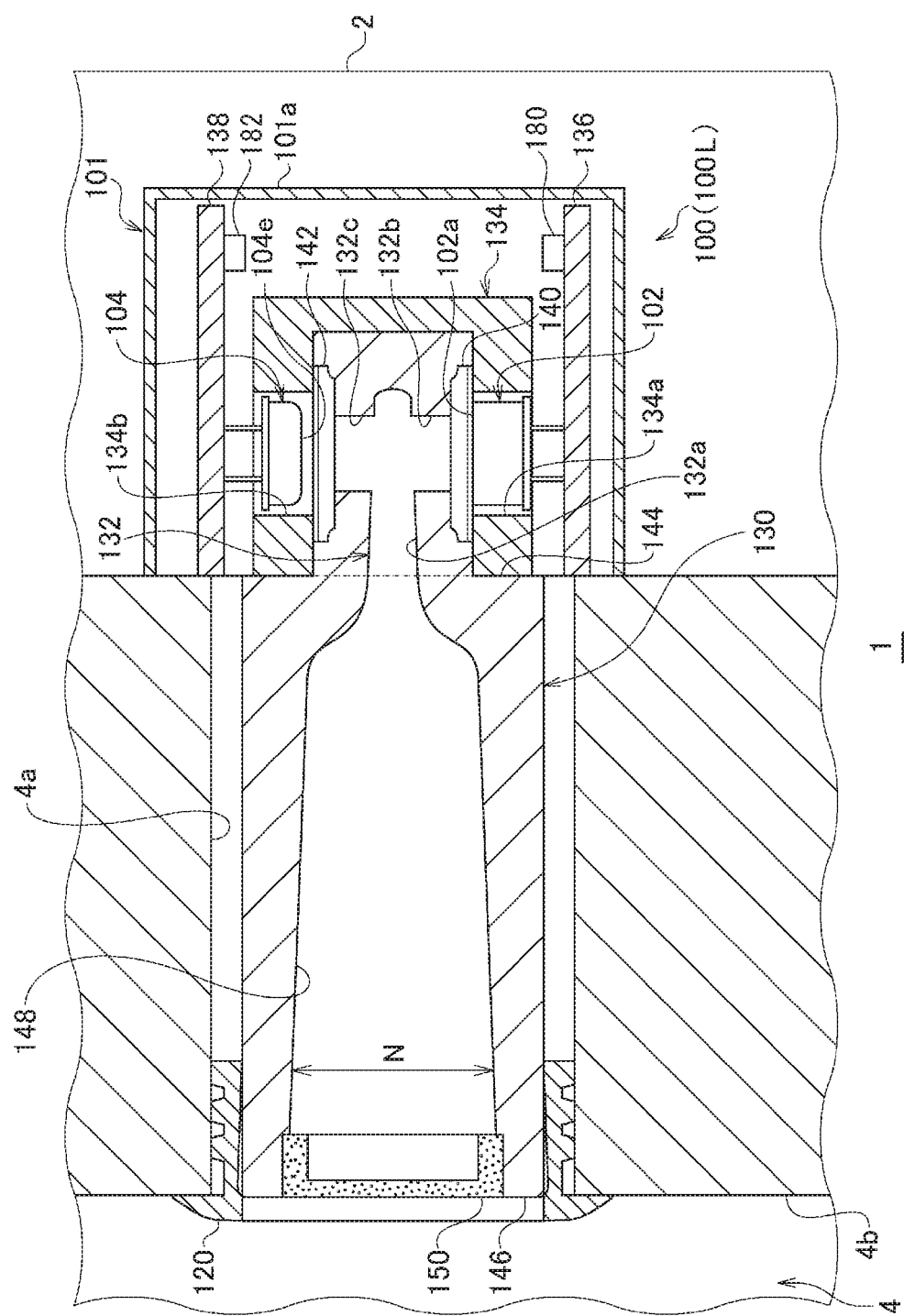
FIG. 9 is a horizontal cross-sectional view showing a gas sensor according to embodiment 6.

FIG. 9 is a horizontal cross-sectional view showing a gas sensor according to embodiment 6. Those features of the gas sensor according to this embodiment that are different from those of embodiment 1 mainly be described. Those features that are common to embodiment 1 will be described briefly, or a description thereof will be omitted.

The gas sensor 100 (100L) according to this embodiment is provided with the gas detection unit 101 including the light source 102, the detector 104, and the gas introduction chamber 132, and with the gas passage 130. The gas passage 130 includes the first end 144, the second end 146, and the hollow part 148. The first end 144 is provided toward the gas detection unit 101, and the second end 146 is provided toward the constant-temperature tank 4. The gas passage 130 circulates the gas subject to detection between the constant-temperature tank 4 and the gas detection unit 101 via the hollow part 148. The hollow part 148 has a shape in which the cross-sectional area N of the flow passage grows smaller away from the second end 146 and toward the first end 144.

The light source 102 is mounted on a substrate 136 and is electrically connected to a wiring pattern (not shown) on the substrate 136. Further, a heating element 180 is mounted on the substrate 136. The heating element 180 is exemplified by a resistor that generates heat of a predetermined temperature when energized. The heating element 180 is provided in the neighborhood of the first lid member 140 and is electrically connected to the wiring pattern on the substrate 136. The heat of the heating element 180 heats the first lid member 140 and the second lid member 142.

The detector 104 is mounted on the substrate 138 and is electrically connected to a wiring pattern (not shown) on the substrate 138. Further, a heating element 182 is mounted on the substrate 138. The heating element 182 is made of a resistor similar to that of the heating element 180. The heating element 182 is provided in the neighborhood of the second lid member 142 and is electrically connected to the wiring pattern on the substrate 138. The heat of the heating element 182 heats the first lid member 140 and the second lid member 142.

By using the heating elements 180, 182 to heat the first lid member 140 and the second lid member 142, dew condensation on the first lid member 140 and the second lid member 142 is inhibited. By inhibiting dew condensation, the efficiency of light guidance from the light source 102 to the detector 104 is inhibited from being lowered, and the accuracy of detection by the gas sensor 100 is further increased. By using the heating elements 180, 182, the size of the gas sensor 100 is reduced as compared to the case of providing a heater. Since the first lid member 140 and the second lid member 142 are heated locally, the power consumption of the gas sensor 100 can be reduced. Further, by mounting the heating element 180 on the same substrate 136 that the light source 102 is mounted on and mounting the heating element 182 on the same substrate 138 that the detector 104 is mounted on, the size and the number of components of the gas sensor 100 are reduced.

The detector 104 is a device in which the output is subject to fluctuation due to the temperature around. For example, the output from a thermopile exemplifying the detector 104 is known to be subject to fluctuation due to the structure thereof. More specifically, a detecting element formed by a thermopile has a seat and a thin film part thermally isolated from the seat. The thin film part functions as a detection unit in which the temperature rises as a result of absorbing infrared light. The detecting element detects an electromotive force generated by a temperature difference between the seat and the thin film part, using the seat as a cold junction, i.e., a reference temperature. For this reason, temperature variation in the seat and in the wiring thermally connected to the seat affects the output of the detecting element greatly. Normally, the output fluctuation is addressed by providing an adiabatic member between the substrate and the detecting element to inhibit the heat of the substrate from being conducted to the detecting element.

In this embodiment, however, the substrate 138 is heated by the heating element 182. Therefore, the adiabatic member alone may not be able to sufficiently inhibit the output fluctuation of the detector 104 due to the heat. We have found through extensive study that the output fluctuation of the detector 104 is inhibited by adjusting a balance between the amount of heat of the heating element 180 and that of the heating element 182.

If the heating element 182 on the side of the detector 104 is provided alone, the signal intensity of the detector 104 tends to be decreased with passage of time. This is considered to be because the temperature difference between the detection unit and the cold junction is decreased as a result of an increase in the temperature of the cold junction due to the heating of the substrate 138. When the output of the detector 104 fluctuates due to the variation in ambient temperature, the variation in temperature difference between the cold junction and the detection unit is eliminated with passage of time so that the output fluctuation is eliminated. However, heating by the heating element 182 takes place only locally. For this reason, the variation in temperature difference between the cold junction and the detection unit is hard to be eliminated with passage of time, and the output fluctuation tends to be maintained.

If the heating element 180 on the side of the light source 102 is provided alone, on the other hand, the signal intensity of the detector 104 tends to be increased with passage of time. This is considered to be because the radiation heat caused by an increase in temperature on the side of the light source 102 heats the detection unit of the detector 104 to increase the temperature difference between the cold junction and the detection unit.

Therefore, the output fluctuation of the detector 104 due to the heating by the heating element 180 and the output fluctuation of the detector 104 due to the heating by the heating element 182 can cancel each other by combining the heating by the heating element 180 on the side of the light source 102 and the heating by the heating element 182 on the side of the detector 104. For example, by causing the heating element 180 and the heating element 182 to generate heat and configuring the quantity of heat generated by the heating element 180 to be larger than the quantity of heat generated by the heating element 182, the output fluctuation of the detector 104 is inhibited. The feature realizes stable gas detection. The quantity of heat provided by the heating element 180 and the heating element 182 to the detector 104 is adjusted by the arrangement of the heating elements 180, 182, the thermal insulation properties of the substrates 136, 138 and of the bracket 134, etc.

In this embodiment, the heating element 180 is mounted on the substrate 136, and the heating element 182 is mounted on the substrate 138. For the purpose of inhibiting dew concentration on the first lid member 140 and the second lid member 142, only one of the heating element 180 and the heating element 182 may be provided.

Embodiment 7

Figure 10:
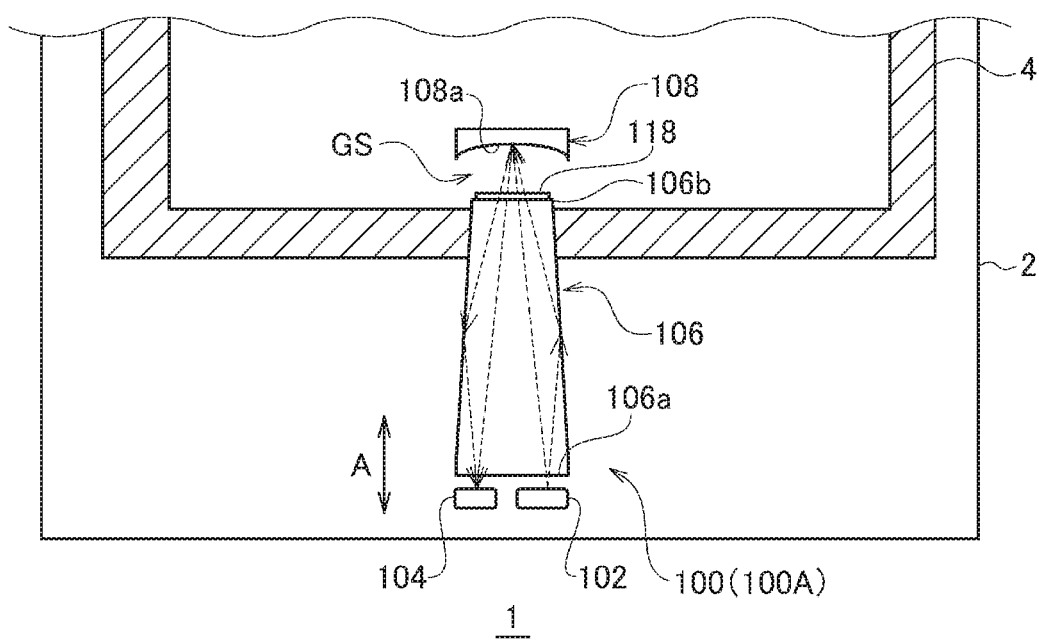
FIG. 10 is a cross-sectional view schematically showing a part of a constant-temperature apparatus according to embodiment 7.
Figure 11:
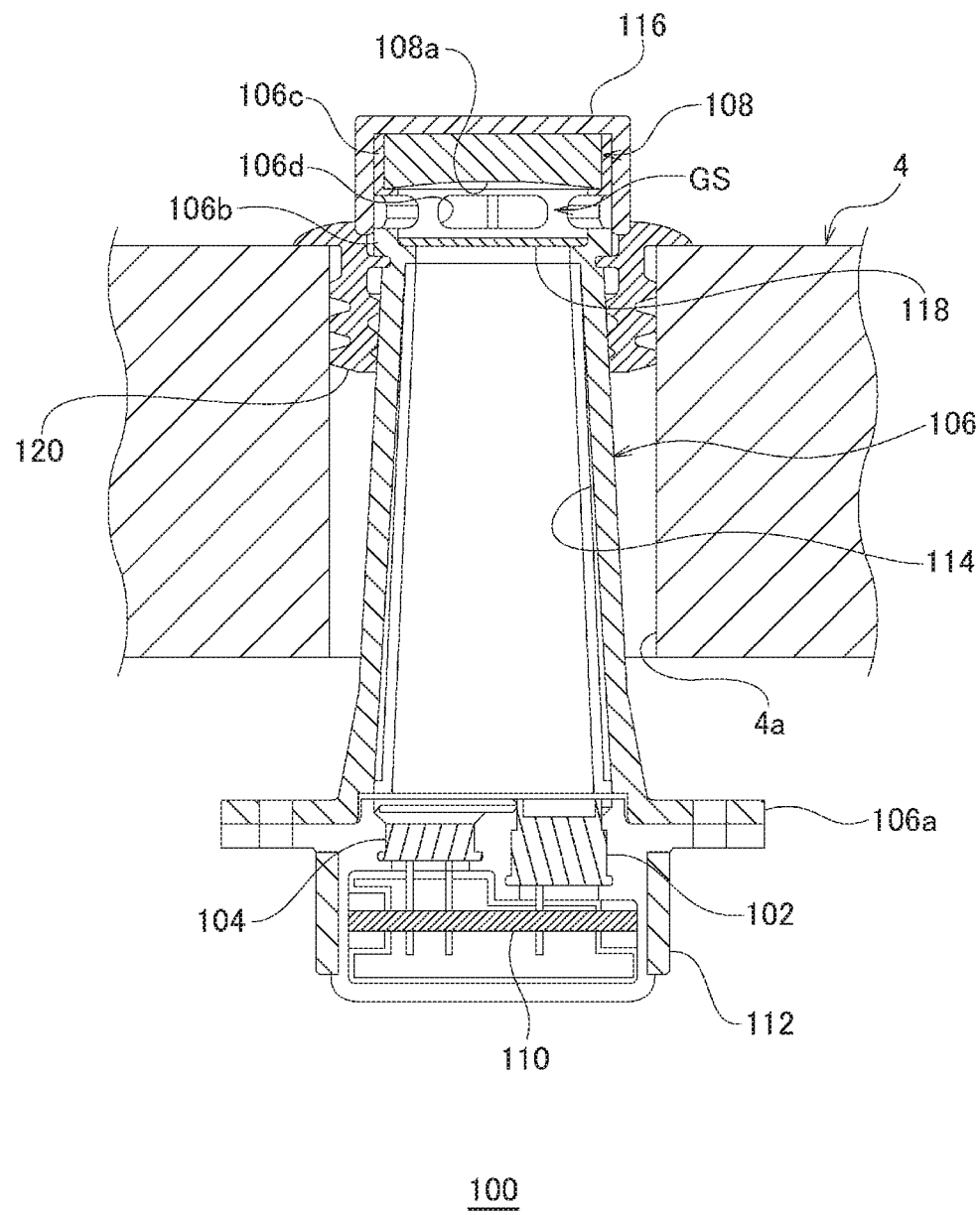
FIG. 11 is a cross-sectional view showing the structure of a gas sensor according to embodiment 7.

FIG. 10 is a cross-sectional view schematically showing a part of a constant-temperature apparatus according to embodiment 7. FIG. 11 is a cross-sectional view showing the structure of a gas sensor according to embodiment 7. The constant-temperature apparatus 1 according to this embodiment is provided with a casing 2, a constant-temperature tank 4, and a gas sensor 100 (100A). The constant-temperature apparatus 1 according to this embodiment is exemplified by a $CO_2$ incubator provided with a dry-heat sterilization function. The casing 2 forms the outer casing of the constant-temperature apparatus 1. The constant-temperature tank 4 is provided inside the casing 2. The constant-temperature tank 4 houses a culture such as cells. The constant-temperature apparatus 1 is configured such that the culture can be transported into or retrieved from an outer door (not shown) provided in the casing 2 and an inner door (not shown) provided in the constant-temperature tank 4. The constant-temperature tank 4 houses a gas (hereinafter, referred to as a tank gas) containing carbon dioxide ($CO_2$), etc.

The gas sensor 100 is a sensor for detecting a gas (hereinafter, referred to as a gas subject to detection) in the constant-temperature tank 4. The gas subject to detection in this embodiment is exemplified by $CO_2$. The gas sensor 100 is capable of detecting the presence and density of the gas subject to detection. The gas sensor 100 transmits a signal indicating the result of detection to the controller (not shown) of the constant-temperature apparatus 1. The gas sensor 100 is inserted into and fixed in a through hole 4a that communicates spaces inside and outside the constant-temperature tank 4. A part of the gas sensor is provided in the interior of the constant-temperature tank 4, and the remainder is provided in the space between the casing 2 and the constant-temperature tank 4. An adiabatic material (not shown) is provided in the space between the casing 2 and the constant-temperature tank 4.

The gas sensor 100 includes a light source 102, a detector 104, a light passage 106, and a light reflecting part 108. The light source 102 emits light of a predetermined wavelength. The light source 102 according to this embodiment is exemplified by a thermal infrared light source comprised of a black-body coating and emits infrared light over an extensive wavelength range. A thermal infrared light source that emits infrared light from a high-temperature heat generator is a mainstream infrared light source. Examples of the heat generator include a filament, a ceramic, and a thin film. An LED may be used in the light source 102.

The detector 104 detects the gas subject to detection based on absorption of light by the gas subject to detection. More specifically, a light receiving device (not shown) of the detector 104 receives the light emitted from the light source 102, and the detector 104 detects the gas subject to detection based on the variation in light intensity caused by the absorption of light by the gas subject to detection. The detector 104 according to this embodiment is exemplified by an infrared sensor configured to absorb infrared light and output an electrical signal. The infrared sensor is exemplified by a quantum type sensor such as a photodiode and a photoconductor configured to output a signal by photoelectric conversion, or a thermal type sensor such as a thermopile and a pyroelectric sensor configured to convert temperature variation due to infrared absorption into an electric signal.

The light source 102 and the detector 104 are mounted on a substrate 110. The light source 102 and the detector 104 are electrically connected to a wiring pattern (not shown) on the substrate 110. The relative positions of the light source 102 and the detector 104 are defined such that the light emitted from the light source 102 does not directly irradiate the light receiving surface of the detector 104. For example, the light receiving surface of the detector 104 is provided in a receded position with respect to the light emitting surface of the light source 102 in the direction of infrared emission. The substrate 110 is supported by a substrate holder 112. If a thermal type sensor such as a thermopile is used as the detector 104, the accuracy of measurement by the detector 104 may be lowered as a result of the heat of the light source 102 being conducted to the detector 104. For this reason, it is favorable to provide an adiabatic member between the detector 104 and the light source 102.

The light passage 106 is a passage for the light emitted from the light source 102. By way of example, the light passage 106 is comprised of a tubular member having a first end 106a and a second end 106b opposite to the first end 106a. The substrate holder 112 is fixed to the first end 106a. Accordingly, the light source 102 and the detector 104 are provided on the side of the first end 106a. The light source 102 is provided such that the emitted light passes through a hollow part of the tubular member. A metal film 114 is formed on the inner surface of the tubular member. The metal film 114 is made of, for example, gold, aluminum, chromium, etc. having a high reflectance in the infrared region. By providing the metal film 114, the light of the light source 102 is inhibited from being absorbed by the light passage 106 and the amount of light received by the detector 104 is inhibited from being lowered.

The light passage 106 includes a light reflecting part holder 106c extending from the second end 106b in a direction opposite to the first end 106a. The light reflecting part holder 106c is tubular, and the light reflecting part 108 is laid in the light reflecting part holder 106c. Further, a cap 116 covers the light reflecting part holder 106c. The cap 116 is made of a porous material having a high heat resistance like polytetrafluoroethylene (PTFE).

When the light reflecting part 108 is laid the light reflecting part holder 106c, a space is formed between the second end 106b and the light reflecting part 108 in the light reflecting part holder 106c. The space constitutes a gas space GS. The gas space GS is a space where the tank gas containing the gas subject to detection is located and so is an area of measurement of the gas subject to detection. The light reflecting part holder 106c includes, at a position corresponding to the gas space GS, an opening 106d that establishes communication between the space outside the gas sensor 100 and the interior of the light reflecting part holder 106c. The tank gas can enter the gas space GS through the opening 106d.

Therefore, the light reflecting part 108 is provided at the second end 106b of the light passage 106 so as to sandwich the gas space GS. The light reflecting part 108 includes a concave reflecting surface 108a. The concave reflecting surface 108a is provided to face the hollow part of the light passage 106. This causes the concave reflecting surface 108a to be opposite to the light source 102 and the detector 104. The concave reflecting surface 108a is formed by, for example, forming a film of metal such as gold, aluminum, chromium, etc. having a high reflectance in the infrared region on the surface of the light reflecting part 108.

A lid member 118 is provided at the second end 106b. The lid member 118 blocks the opening in the light passage 106 toward the second end 106b. The lid member 118 is made of a material that transmits the light emitted by the light source 102 (i.e., the ratio of absorption of emitted light is low). In this embodiment, infrared light is emitted from the light source 102. Therefore, the lid member 118 is made of, for example, germanium, silicon, sapphire, etc. By providing the lid member 118, the tank gas located in the gas space GS is inhibited from entering the light passage 106. Therefore, the distance between the concave reflecting surface 108a and the lid member 118 represents a distance (optical distance) provided for measurement of the gas subject to detection by the light emitted from the light source 102.

The gas sensor 100 is fixed relative to the constant-temperature tank 4 by laying the packing 120 between the outer side surface of the light passage 106 and the inner side surface of the through hole 4a while the light passage 106 is being inserted into the through hole 4a of the constant-temperature tank 4. For example, the packing 120 is made of a silicon resin. The gas sensor 100 is configured such that the opening 106d of the light passage 106 is located in the constant-temperature tank 4, and the light source 102 and the detector 104 are located outside the constant-temperature tank 4.

In the gas sensor 100 provided with the above-described features, the light emitted from the light source 102 arrives at the light reflecting part 108 via the light passage 106 and the gas space GS. The light is reflected by the concave reflecting surface 108a of the light reflecting part 108 and arrives at the detector 104 via the gas space GS and the light passage 106. More specifically, the light of the light source 102 enters the hollow part of the light passage 106 from the first end 106a and arrives at the second end 106b either directly or by being reflected by the metal film 114. The light enters the gas space GS by passing through the lid member 118. The light traveling in the gas space GS is reflected by the concave reflecting surface 108a and enters the hollow part of the light passage 106 again via the gas space GS and the lid member 118. The light entering the hollow part arrives at the detector 104 either directly or by traveling toward the first end 106a as it is reflected by the metal film 114.

The light emitted from the light source 102 passes through the gas space GS in the process of arriving at the detector 104 from the light source 102. During the passage, the light of a predetermined wavelength is absorbed by the gas subject to detection located in the gas space GS. In this embodiment, the light source 102 emits infrared light, and the light of a wavelength 4.26 μm is absorbed by $CO_2$ located in gas space GS. The detector 104 can detect the presence and density of $CO_2$ located in the gas space GS based on the intensity (amount of light) of the light of the wavelength 4.26 μm in the light received by the light receiving device, with reference to the intensity (amount of light) of the light of the wavelength 4.26 μm in the light emitted from the light source 102. For example, the density of $CO_2$ that the gas sensor 100 is capable of detecting is 0~20%.

Since the gas sensor 100 is provided with the light passage 106, the light source 102 and the detector 104 are isolated from the gas space GS. Therefore, exposure of the light source 102 and the detector 104 to the tank gas is avoided. Conduction of the heat from an internal space of the constant-temperature tank 4 to the light source 102 and the detector 104 is also inhibited. As a result, damage to the light source 102 and the detector 104 from the heat is inhibited so that the accuracy of detection by the gas sensor 100 is inhibited from being lowered.

The shape of the light passage 106, the arrangement of the light source 102, the detector 104, and the light reflecting part 108, and the material for the light passage 106 according to this embodiment will be described below in further detail.

Figure 12A:
FIG. 12A schematically shows the shape of the first end and the second end.
Figure 12B:
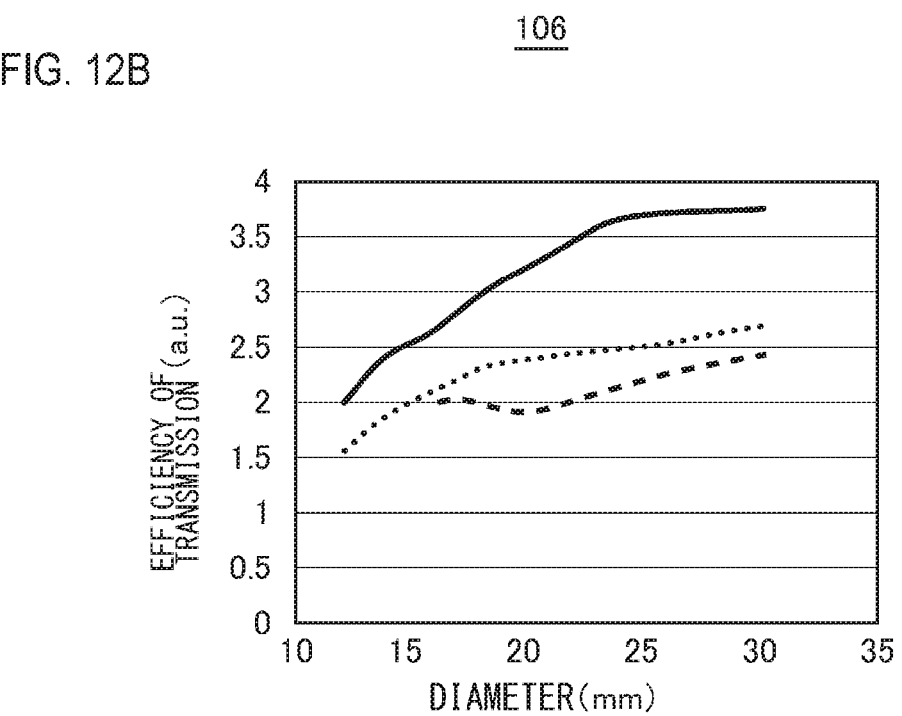
FIGS. 12B and 12C are graphs showing the relationship between the shape of the light passage and the efficiency of light transmission from the light source to the detector.
Figure 12C:
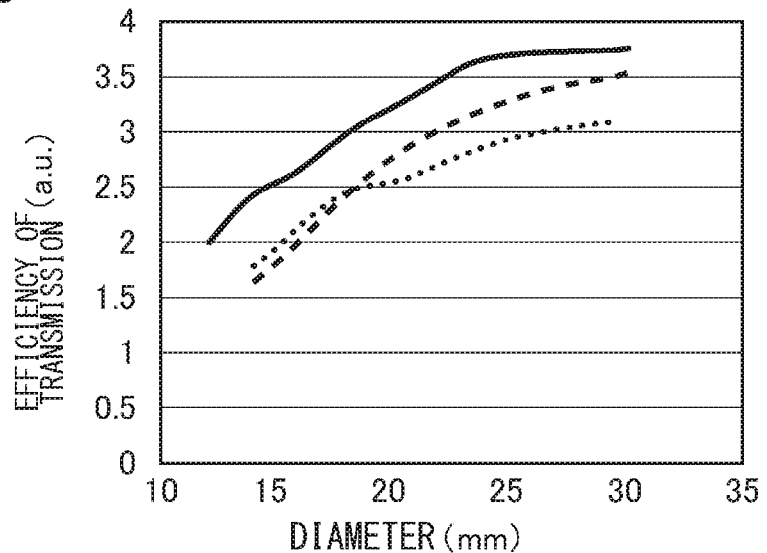

FIG. 12A schematically shows the shape of the first end 106a and the second end 106b. FIGS. 12B and 12C are graphs showing the relationship between the shape of the light passage 106 and the efficiency of light transmission from the light source 102 to the detector 104. For measurement of the transmission efficiency for which the result is shown in FIG. 12B, a first light passage in which the first end 106a is elliptical and the second end 106b is circular, a second light passage configured as a circular tube (i.e., the first end 106a and the second end 106b are both circular), and a third light passage configured as an elliptical tube (i.e., the first end 106a and the second end 106b are both elliptical) were prepared.

With regard to the first light passage, the relationship between the diameter of the circle of the second end 106b and the transmission efficiency was measured, varying the diameter. The long diameter and the short diameter of the ellipse were fixed to 16 mm and 8 mm, respectively. This is the minimum size of the ellipse that covers the light emitting surface of the light source 102 and the light receiving surface of the light receiving device included in the detector 104. Excluding the efficiency of light transmission between the light source 102 and the light reflecting part 108 and between the light reflecting part 108 and the detector 104 from consideration and considering only the transmission efficiency on a plane including the first end 106a, the smaller the area of the ellipse, the higher the efficiency of light transmission. The result is indicated in FIG. 12B by a solid line. With regard to the second light passage, the relationship between the diameter of the circle and the transmission efficiency was measured, varying the diameter. The result is indicated in FIG. 12B by a dotted line. With regard to the third light passage, the relationship between the long diameter of the ellipse and the transmission efficiency was measured, varying the long diameter. The ratio between the long diameter and the short diameter of the ellipse was fixed to 2:1. The result is indicated in FIG. 12B by a broken line.

For measurement of the transmission efficiency for which the result is shown in FIG. 12C, a first light passage in which the first end 106a is elliptical and the second end 106b is circular, a fourth light passage configured as a truncated cone (i.e., the first end 106a and the second end 106b are both circular), and a fifth light passage configured as a truncated elliptical cone (i.e., the first end 106a and the second end 106b are both elliptical) were prepared.

With regard to the first light passage, the relationship between the diameter of the circle of the second end 106b and the transmission efficiency was measured, varying the diameter. The result is indicated in FIG. 12C by a solid line. With regard to the fourth light passage, the relationship between the diameter of the circle of the second end 106b and the transmission efficiency was measured, varying the diameter. The result is indicated in FIG. 12C by a solid line. With regard to the fifth light passage, the relationship between the long diameter of the ellipse of the second end 106b and the transmission efficiency was measured, varying the long diameter. The ratio between the long diameter and the short diameter of the ellipse was fixed to 2:1. The result is indicated in FIG. 12C by a broken line. The long diameter and the short diameter of the ellipse of the first end 106a in the first light passage and the fifth light passage were fixed to 16 mm and 8 mm, respectively. The diameter of the circle of the first end 106a in the fourth light passage was fixed to 16 mm. The sizes of the ellipse and the circle are minimum sizes that cover the light emitting surface of the light source 102 and the light receiving surface of the light receiving device included in the detector 104.

Both in the measurement for which the result is shown in FIG. 12B and the measurement for which the result is shown in FIG. 12C, the distance between the light source 102 and the detector 104 was fixed to 10 mm. The diameter of the concave reflecting surface 108a is configured to be sufficiently larger than the maximum permitted value of the diameter of the second end 106b. The transmission efficiency was defined by the amount of light of the wavelength 4.26 μm in the light received by the light receiving device, with reference to the amount of light of the wavelength 4.26 μm in the light emitted from the light source 102, i.e., the proportion of the light from the light source 102 received by the detector 104 (the unit is an arbitrary unit: a. u.).

As shown in FIG. 12A, the first end 106a of the light passage 106 of the gas sensor 100 according to this embodiment is elliptical, and the second end 106b is circular. In particular, the inner side surface of the first end 106a (the surface provided with the metal film 114) is elliptical, and the inner side surface of the second end 106b is circular. Further, the light passage 106 has a shape that changes progressively from elliptical to circular from the first end 106a to the second end 106b. As shown in FIG. 12B, the light passage 106 in which the first end 106a is elliptical and the second end 106b is circular tends to provide improved transmission efficiency over the light passage in which both ends are circular or elliptical. Further, as shown in FIG. 12C, the light passage 106 in which the first end 106a is elliptical and the second end 106b is circular tends to provide improved transmission efficiency over the light passage shaped in a truncated cone or a truncated elliptical cone. Therefore, the accuracy of the gas sensor 100 is further improved, and the detector 104 is further simplified. In further accordance with the feature, the diameter of the light passage 106 is reduced, while also inhibiting the transmission efficiency from being lowered. The result shown in FIG. 12C also reveals that the smaller the area of the first end 106a relative to the area of the second end 106b, the further the transmission efficiency is improved. It is therefore preferable that the area of the first end 106a be as small as possible, providing that consideration should be given to the arrangement of the light source 102 and the detector 104 and the area of the light emitting surface and the light receiving surface aligned with the first end 106a.

Figure 13:
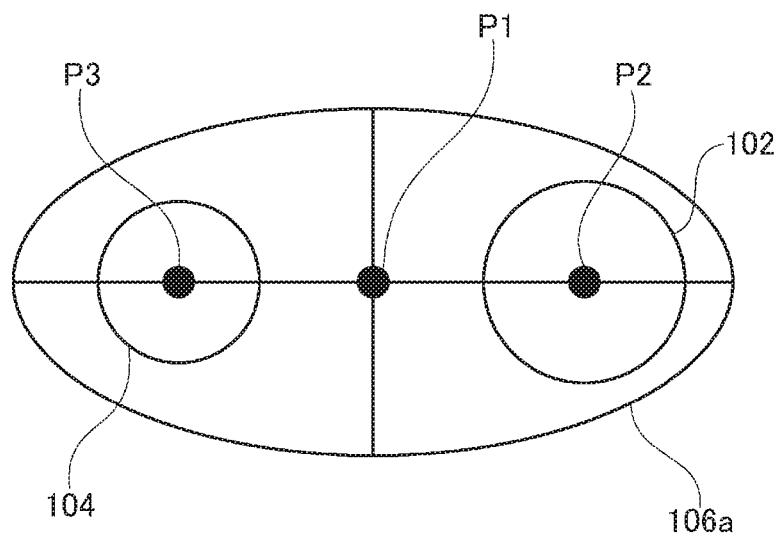
FIG. 13 is a schematic diagram showing the arrangement of the light source and the detector.

FIG. 13 is a schematic diagram showing the arrangement of the light source 102 and the detector 104. Where the first end 106a of the light passage 106 is configured to be elliptical, it is preferable that the light source 102 and the detector 104 are arranged at positions point-symmetric with respect to a center P1 of the ellipse when viewed in the direction in which the light source 102/the detector 104, and the light passage 106 are arranged (the direction indicated by an arrow A in FIG. 10), as shown in FIG. 13. In this case, arbitrary parts of the light source 102 and the detector 104 are provided at point-symmetric positions by way of example. Alternatively, a center P2 of the light emitting part of the light source 102 and a center P3 of the light receiving surface of the detector 104 (e.g., the surface observed from the light reflecting part 108 in the direction of the arrow A of FIG. 10) are provided at point-symmetric positions. The feature allows the light emitted from the light source 102 to be focused on the detector 104 more properly. Accordingly, the efficiency of light transmission from the light source 102 to the detector 104 is improved. The center P1 of the ellipse is the intersection of the long axis and the short axis of the ellipse.

Further, the light source 102 and the detector 104 are more preferably provided on the long diameter of the ellipse. Still more preferably, the light source 102 is provided on one focal point of the ellipse, and the detector 104 is provided on the other focal point of the ellipse. These features further improves the efficiency of light transmission.

Figure 14:
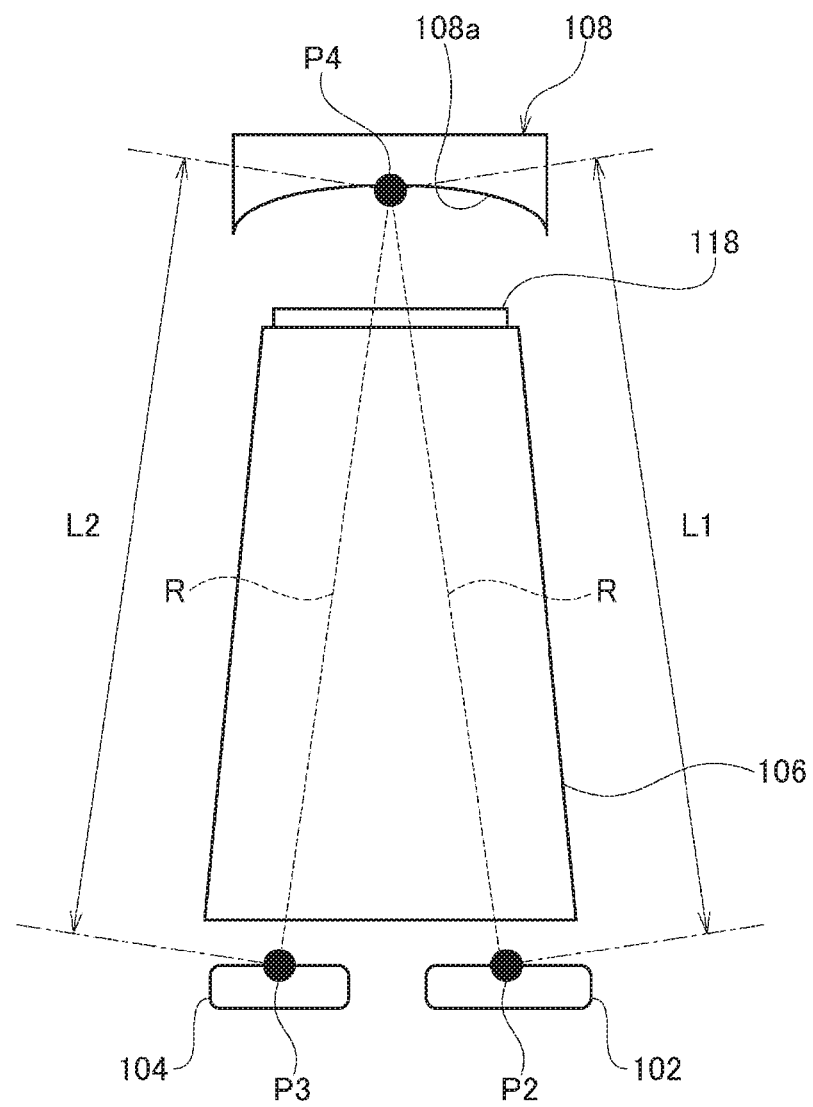
FIG. 14 is a schematic diagram illustrating the arrangement of the light source, the detector, and the light reflecting part.

FIG. 14 is a schematic diagram illustrating the arrangement of the light source 102, the detector 104, and the light reflecting part 108. As shown in FIG. 14, the concave reflecting surface 108a according to this embodiment has a predetermined radius of curvature R. The light source 102, the detector 104, and the light reflecting part 108 are provided such that a distance L1 between the concave reflecting surface 108a and the light source 102 and a distance L2 between the concave reflecting surface 108a and the detector 104 meet conditions R×0.9≤L1, L2≤R×1.1. In this case, the distance from an arbitrary part of the light emitting part of the light source 102 to a center P4 of the concave reflecting surface 108a or the distance from the center P2 of the light emitting part to the center P4 is defined as the distance L1. Further, the distance from an arbitrary part of the light receiving surface of the detector 104 to the center P4 or the distance from the center P3 of the light receiving surface to the center P4 is defined as the distance L2.

Thus, by approximating the distances L1, L2 to the radius of curvature R of the concave reflecting surface 108a, the light source 102 and the detector 104 are in a confocal arrangement with respect to the concave reflecting surface 108a in a direction in which the light travels from the light source 102 to the concave reflecting surface 108a or a direction in which the light travels from the concave reflecting surface 108a to the detector 104 (i.e., the direction of light propagation). The feature allows the light emitted from the light source 102 to be focused on the detector 104 more properly. As a result, the efficiency of guiding the light from the light source 102 to the detector 104 is improved.

Further, the light source 102, the detector 104, and the light reflecting part 108 may be provided such that at least one of the distance L1 and the distance L2 is not less than R×0.9 and less than R, or more than R and not more than R×1.1. In other words, at least one of the distances L1, L2 (denoted by L) meets a condition R×0.9≤L<R, or R<L≤R×1.1. In other words, the distance L1 and/or the distance L2 is defined to have a value near the radius of curvature R and not equal to the radius of curvature R. Thus, by shifting at least one of the light source 102 and the detector 104 slightly from the focal position of the concave reflecting surface 108a, the radius of the spot of the focused light on the light receiving surface of the detector 104 is configured to be larger than when the distance L1 and the distance L2 are equal to the radius of curvature R, i.e. the spot of the focused light is blurred. The feature secures the efficiency of light transmission and inhibits the output fluctuation of the detector 104 in the presence of mechanical fluctuations in parts constituting the gas sensor 100, etc. from growing.

By placing the light source 102 and the detector 104 at the focal positions of the ellipse at the first end 106a and approximating the distances L1, L2 as far as the concave reflecting surface 108a to the radius of curvature R, the light source 102 and the detector 104 are placed in a confocal arrangement both within the elliptical plane and in the direction of light propagation. The feature increases the efficiency of light transmission from the light source 102 to the detector 104 is significantly.

Figure 15A:
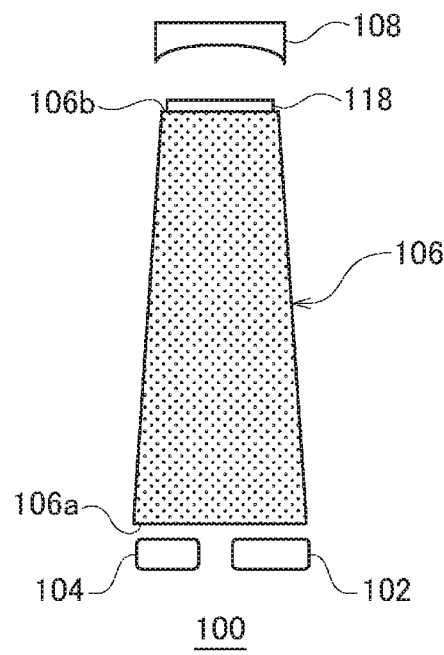
FIGS. 15A and 15B are schematic diagrams illustrating the material of the light passage.
Figure 15B:
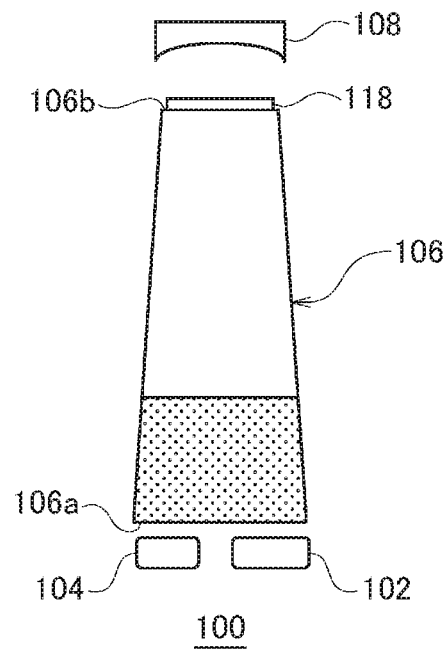

FIGS. 15A and 15B are schematic diagrams illustrating the material of the light passage 106. In FIGS. 15A and 15B, the part made of an adiabatic material is patterned. As shown in FIG. 15A, the light passage 106 according to this embodiment is made of an adiabatic material in its entirety. Alternatively, only a part of the light passage 106 may be made of an adiabatic material, as shown in FIG. 15B. In this case, it is preferable to provide the adiabatic material such that the non-adiabatic material is discontinuous at some position between the first end 106a and the second end 106b.

By configuring at least a part of the light passage 106 to be made of an adiabatic material, the heat in the internal space of the constant-temperature tank 4 is inhibited from being conducted to the light source 102 and the detector 104 via the light passage 106. For example, a material that causes the neighborhood of the light source 102 and the detector 104 to be at a temperature of 100° C. or lower when the temperature inside the constant-temperature tank 4 is 190° C. is selected. By selecting an adiabatic material having a high heat resistance, the adiabatic effect is enhanced. A high-temperature resistant resin is suitable as the adiabatic material. This is because a high-temperature resistant resin can be worked more easily and is more heat resistant than a metal. Specific examples of the adiabatic material include: polyphenylene sulfide (PPS); a fluororesin like polytetrafluoroethylene (PTFE) and Teflon (registered trademark); polyether ether ketone (PEEK); silicon resin; and polyamide-imide (PAI). Configuring the light passage 106 to be hollow is useful in enhancing the adiabatic effect.

As described above, the gas sensor 100 according to this embodiment is provided with the light source 102, the detector 104 for detecting the gas subject to detection based on absorption of light by the gas subject to detection, the light passage 106, and the light reflecting part 108. The light source 102 and the detector 104 are provided at the first end 106a of the light passage 106, and the light reflecting part 108 is provided at the second end 106b opposite to the first end 106a so as to sandwich the gas space GS. The light emitted from the light source 102 passes through the light passage 106 and the gas space GS, is reflected by the light reflecting part 108, and passes through the gas space GS and the light passage 106 again to be received by the detector 104. The light of a predetermined wavelength included in the light emitted from the light source 102 is absorbed by the gas subject to detection as it passes through the gas space GS. The detector 104 can detect the presence and density of the gas subject to detection based on the variation in the amount of light of the predetermined wavelength.

The gas sensor 100 has an area of measurement of the gas subject to detection at an end toward the light reflecting part 108. Only this end is inserted into a closed space filled with the tank gas. The light source and the detector 104 are spaced apart by the light passage 106 from the area of measurement of the gas subject to detection. The feature inhibits conduction of heat to the light source 102 and the detector 104 when the temperature of the area of measurement of the gas subject to detection is high, such as when the temperature of the tank gas exceeds the withstand temperature of the light source 102 and the detector 104 or when the space filled with the tank gas is sterilized by dry sterilization. Therefore, the accuracy of detection by the gas sensor 100 is inhibited from being lowered. The light passage 106 is made of an adiabatic material at least in part. This further inhibits the accuracy of detection by the gas sensor 100 from being lowered.

The light passage 106 according to this embodiment is comprised of a tubular member, and the lid member 118 is provided at the second end 106b toward the gas space GS. The feature inhibits the tank gas located in the gas space GS from entering the hollow part of the light passage 106. If the tank gas in the gas space GS enters the light passage 106, the light is absorbed by the gas subject to detection inside the light passage 106, too. Accordingly, the accuracy of detection of the gas subject to detection may be lowered. Therefore, by providing the lid member 118, the gas subject to detection is detected with a higher accuracy. Further, if the tank gas flows into the light passage 106, the convection flow of the tank gas causes the response speed of the detector 104 in response to the variation in the density of the gas subject to detection to be lowered. Therefore, by providing the lid member 118, the speed of detection of the gas subject to detection is improved.

Further, the light passage 106 is elliptical at the first end 106a where the light source 102 and the detector 104 are provided and is circular at the second end 106b where the light reflecting part 108 is provided. The feature increases the efficiency of light emission from the light source 102 to the detector 104 and so increases the accuracy of the gas sensor 100. The efficiency of light transmission can be improved by providing an optical member such as a lens on the light path. However, addition of an optical member increases the number of components of the gas sensor 100. Since an optical member that transmits infrared light is expensive, the manufacturing cost of the gas sensor 100 will be increased in the case the light source 102 is configured to emit infrared light. By way of contrast, this embodiment is configured to improve the efficiency of light transmission by shaping the light passage 106 properly so that the number of components of the gas sensor 100 and the manufacturing cost are prevented from increasing.

The light source 102 and the detector 104 are provided at positions point-symmetric with respect to the center P1 of the elliptical shape at the first end 106a. Further, the distance L1 between the concave reflecting surface 108a of the light reflecting part 108 and the light source 102 and the distance L2 between the concave reflecting surface 108a and the detector 104 are accommodated in a range from 90% to 110% of the radius of curvature R of the light reflecting part 108. These features further increase the efficiency of light transmission. Further, at least one of the distance L1 and the distance L2 may be configured to be in a range from 90% to 110% of the radius of curvature R and not to be identical with the radius of curvature R. The feature secures the efficiency of light transmission and reduces the output fluctuation of the detector 104 caused by mechanical fluctuations in parts of the gas sensor 100, etc.

By mounting the gas sensor 100 on the constant-temperature apparatus 1, the usability and performance of the constant-temperature apparatus 1 are further improved.

Embodiment 8

Figure 16:
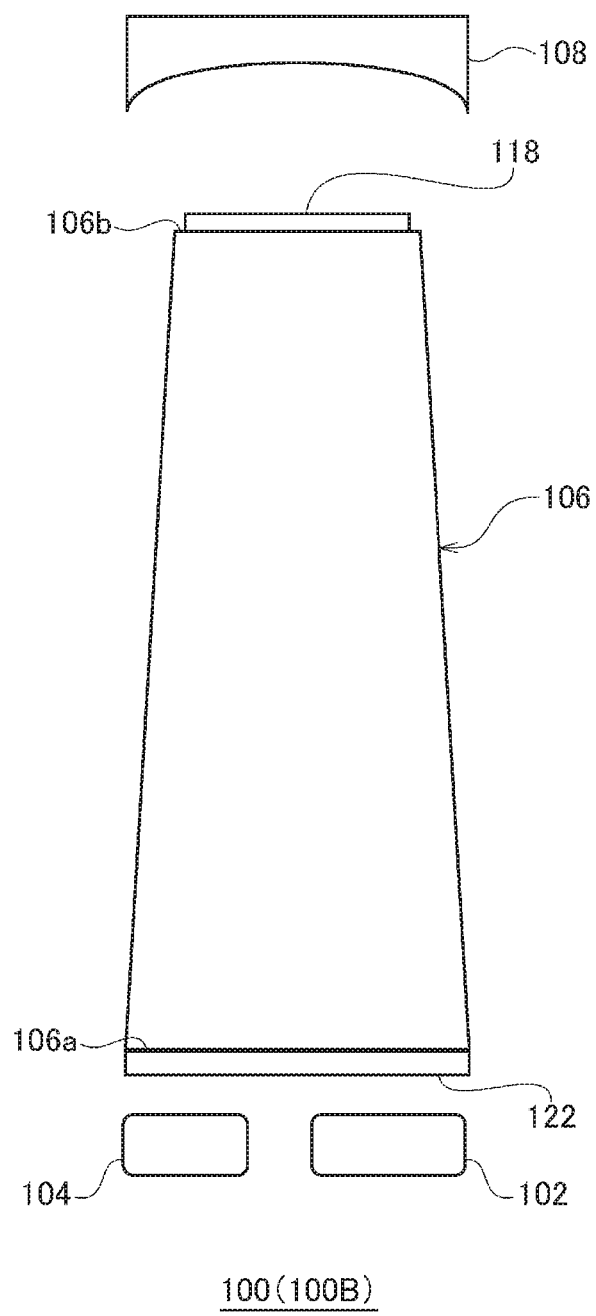
FIG. 16 is a side view schematically showing a gas sensor according to embodiment 8.

The gas sensor according to embodiment 8 has a configuration which is common to that of embodiment 7 except that a lid member that blocks the opening at the first end 106a is further provided. Those features of the gas sensor according to this embodiment that are different from those of embodiment 7 will mainly be described. Common features will be described briefly, or a description thereof will be omitted. FIG. 16 is a side view schematically showing a gas sensor according to embodiment 8.

The gas sensor 100 (100B) according to this embodiment includes a light source 102, a detector 104, a light passage 106, a light reflecting part 108, a lid member 118, and a lid member 122. The light passage 106 is comprised of a tubular member. The light source 102 is provided such that the light passes through the hollow part of the tubular member. The lid member 118 is provided at the second end 106b of the light passage 106. The lid member 122 is provided at the first end 106a of the light passage 106.

The lid member 122 blocks the opening in the light passage 106 toward the first end 106a. Like the lid member 118, the lid member 122 is made of a material that transmits the light emitted by the light source 102. In the constant-temperature apparatus 1 provided with the gas sensor 100, the ambient gas located around the constant-temperature apparatus 1 flows into the space between the casing 2 and the constant-temperature tank 4. Therefore, if the lid member 122 is not provided at the first end 106a of the light passage 106, the ambient gas around the constant-temperature apparatus 1 can enter the hollow part of the light passage 106 from the opening at the first end 106a.

Meanwhile, if the outer door and the inner door of the constant-temperature apparatus 1 are opened, the tank gas containing the gas subject to detection leaks outside and is diffused in the ambient gas. This changes the density of the gas subject to detection in the ambient gas. If the lid member 122 is not provided in the opening toward the first end 106a, a change in the density of the gas subject to detection in the ambient gas can change the density of the gas subject to detection in the light passage 106. The change in the density of the gas subject to detection in the light passage 106 can cause a measurement error and make it difficult to detect the density of the gas subject to detection accurately.

By way of contrast, the gas sensor 100 according to this embodiment is provided with the lid member 122 that blocks the opening at the first end 106a. Therefore, the ambient gas around the constant-temperature apparatus 1 is inhibited from entering the hollow part of the light passage 106. Accordingly, the gas subject to detection located in the gas space GS is detected in a stable manner and with a high accuracy even if the density of the gas subject to detection in the ambient gas changes.

Embodiment 9

Figure 17:
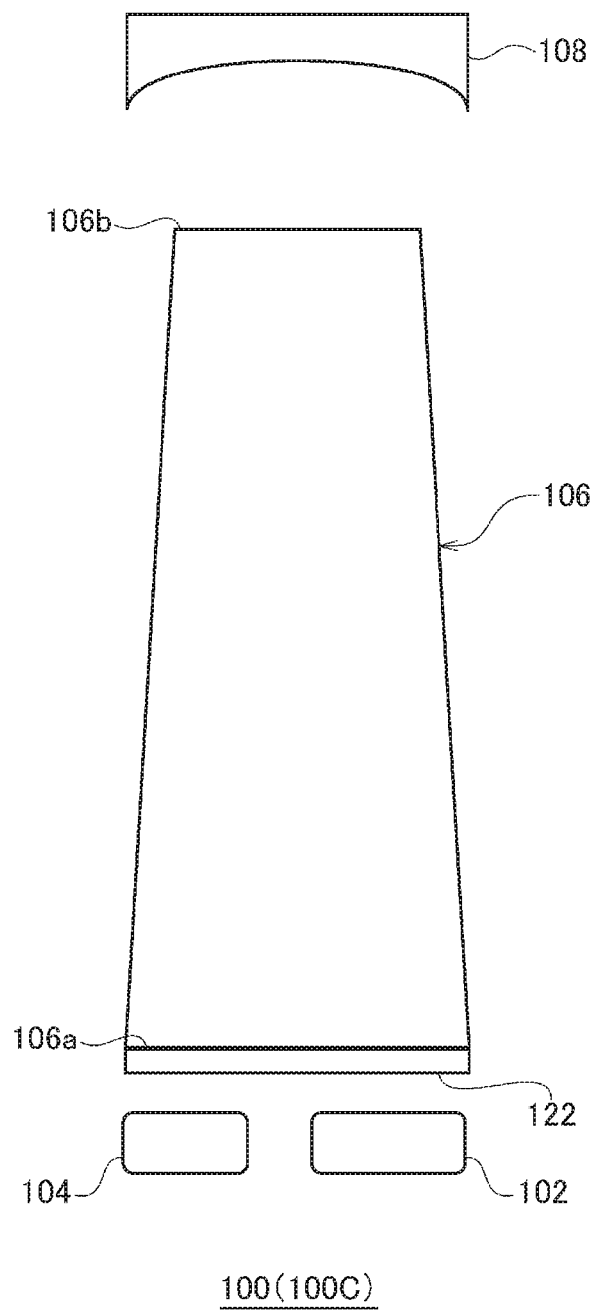
FIG. 17 is a side view schematically showing a gas sensor according to embodiment 9.

The gas sensor according to embodiment 9 has a configuration which is common to that of embodiment 7 except that only a lid member 122 that blocks the opening at the first end 106a is provided in place of the lid member 118. Those features of the gas sensor according to this embodiment that are different from those of embodiment 7 will mainly be described. Common features will be described briefly, or a description thereof will be omitted. FIG. 17 is a side view schematically showing a gas sensor according to embodiment 9.

The gas sensor 100 (100C) according to this embodiment includes a light source 102, a detector 104, a light passage 106, a light reflecting part 108, and a lid member 122. The light passage 106 is made of a tubular member. The light source 102 is provided such that the light passes through the hollow part of the tubular member. The lid member 122 is provided at the first end 106a of the light passage 106. The lid member 122 blocks an opening in the light passage 106 toward the first end 106a. Like the lid member 118, the lid member 12 is made of a material that transmits the light from the light source 102.

The gas sensor 100 according to this embodiment is not provided with the lid member 118, and the opening at the second end 106b is not blocked. Therefore, the tank gas in the gas space GS can enter the hollow part of the light passage 106 from the opening at the second end 106b. The feature extends the distance that the light emitted from the light source 102 passes through the gas space GS, i.e., the distance of measurement of the gas subject to detection. As a result, the gas for which a relatively long distance of measurement is required such as water vapor (H$_2$O) is detected with a higher accuracy. The lid member 122 inhibits the tank gas entering the light passage 106 from leaking outside the constant-temperature apparatus 1.

Embodiment 10

Figure 18:
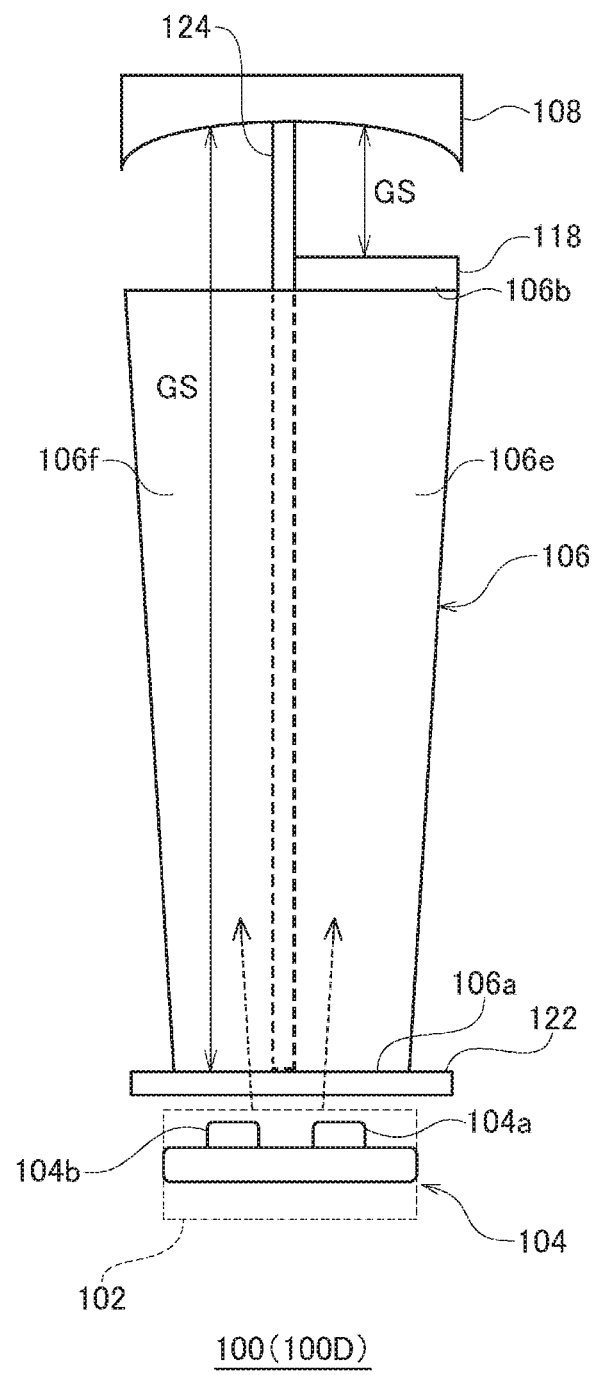
FIG. 18 is a side view schematically showing a gas sensor according to embodiment 10.

The gas sensor according to embodiment 10 differs significantly from embodiment 8 in that a partition member is provided but has a configuration substantially common to that of embodiment 8 in the other respects. Those features of the gas sensor according to this embodiment that are different from those of embodiment 8 will mainly be described. Common features will be described briefly, or a description thereof will be omitted. FIG. 18 is a side view schematically showing a gas sensor according to embodiment 10. FIG. 18 shows the gas sensor observed in a direction displaced by 90° in the circumferential direction of the tube of the light passage 106 with respect to the direction of observation of the gas sensor 100 in FIG. 10. In FIG. 18, the light source 102, which is provided behind the detector 104 in the direction of depth of the paper, is indicated by a broken line.

The gas sensor 100 (100D) according to this embodiment includes a light source 102, a detector 104, a light passage 106, a light reflecting part 108, a lid member 118, a lid member 122, and a partition member 124. The light passage 106 is comprised of a tubular member. The partition member 124 divides the hollow part of the light passage 106 into a first area 106e and a second area 106f. Each of the first area 106e and the second area 106f extends from the first end 106a side to the second end 106b side. The partition member 124 may divide the hollow part of the light passage 106 into at least two areas. Therefore, the partition member 124 may divide the interior of the light passage 106 into three or more areas. One end of the partition member 124 comes into contact with the lid member 122, and the other end comes into contact with the light reflecting part 108.

The lid member 118 blocks the opening in the first area 106e at the second end 106b. The lid member 118 does not block the opening in the second area 106f at the second end 106b. Therefore, the opening in the second area 106f at the second end 106b is not blocked. The lid member 122 blocks the openings in the first area 106e and the second area 106f at the first end 106a.

The light source 102 is provided such that the light passes through the first area 106e and the second area 106f. The detector 104 includes a first detection unit 104a that receives the light passing through the first area 106e and a second detection unit 104b that receives the light passing through the second area 106f. Each of the first detection unit 104a and the second detection unit 104b is a light receiving device.

A portion of the light emitted from the light source 102 passes through the lid member 122, the first area 106e, and the lid member 118 in the stated order and arrives at the light reflecting part 108. The light is reflected by the light reflecting part 108, passes through the lid member 118, the first area 106e, and the lid member 122 in the stated order and arrives at the first detection unit 104a. The other portion of the light emitted from the light source 102 passes through the lid member 122 and the second area 106f in the stated order and arrives at the light reflecting part 108. The light is reflected by the light reflecting part 108, passes through the second area 106f and the lid member 122 in the stated order, and arrives at the second detection unit 104b.

The tank gas is introduced from the opening 106d (see FIG. 11) into the space between the light reflecting part 108 and the second end 106b. Since the lid member 118 is provided in the opening in the first area 106e at the second end 106b, the tank gas cannot enter the first area 106e. Meanwhile, the opening in the second area 106f at the second end 106b is not blocked so that the tank gas can enter the second area 106f. Since the partition member 124 is provided at the boundary between the first area 106e and the second area 106f, the tank gas entering the second area 106f cannot enter the first area 106e.

Therefore, the area between the light reflecting part 108 and the lid member 118 will be a gas space GS, i.e., the area of measurement of the gas subject to detection for the light passing through the first area 106e. Meanwhile, the area between the light reflecting part 108 and the lid member 122 will be a gas space GS for the light passing through the second area 106f. Therefore, the distance of measurement of the gas subject to detection is relatively short for the light passing through the first area 106e, and the distance of measurement of the gas subject to detection is relatively long for the light passing through the second area 106f.

Thus, by using the partition member 124 to form a plurality of areas that differ in the extent of the gas space GS, a plurality of types of gas subject to detection can be detected by a single gas sensor 100. For example, the $CO_2$ density and humidity (i.e., the density of $H_2O$) can be simultaneously measured by the gas sensor 100 according to this embodiment. The suitable distance of measurement of $CO_2$ is shorter than that of $H_2O$ and is, for example, several mm. Meanwhile, the suitable distance of measurement of $H_2O$ is, for example, several cm. Further, the wavelength absorbed by $CO_2$ is 4.26 μm, and the wavelength absorbed by $H_2O$ is 2.5~2.9 μm and 5~7 μm. Accordingly, the first detection unit 104a that receives the light passing through the first area 106e is configured to measure the variation in the intensity of light at the wavelength 4.26 μm. Further, the second detection unit 104b that receives the light passing through the second area 106f is configured to measure the variation in the intensity of light at the wavelength 2.5~2.9 μm. The feature enables simultaneous measurement of the density of $CO_2$ and $H_2O$.

Embodiment 11

Figure 19A:
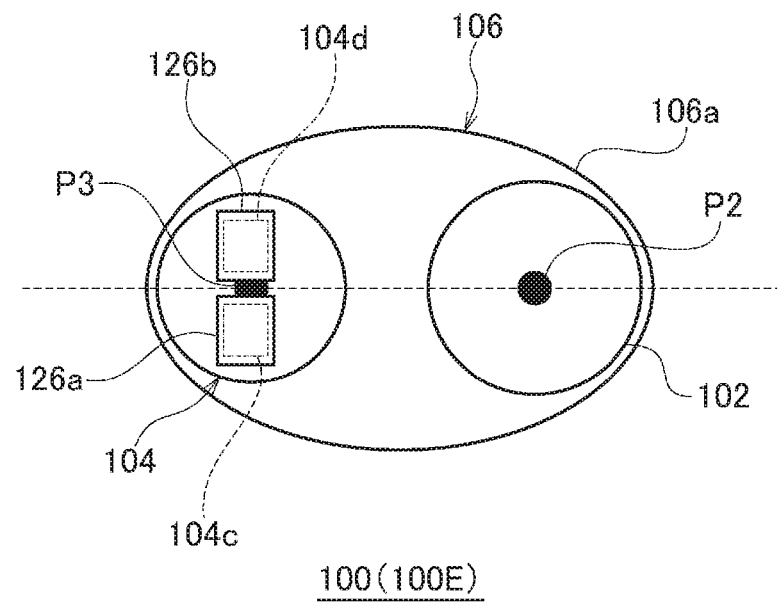
FIG. 19A is a plan view schematically showing a gas sensor according to embodiment 11.
Figure 19B:
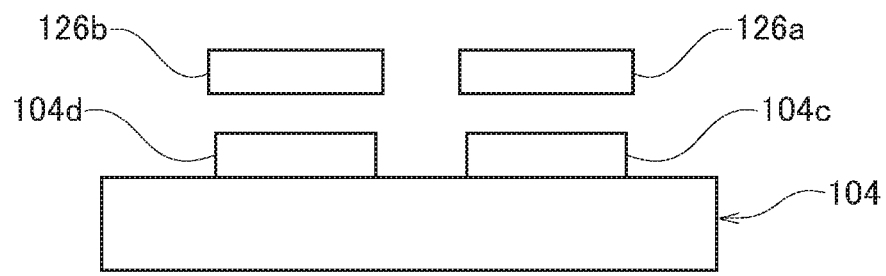

The gas sensor according to embodiment 11 has a configuration substantially common to that of embodiment 7 except that a plurality of detection units and a plurality of optical filters are provided. Those features of the gas sensor according to this embodiment that are different from those of embodiment 7 will mainly be described. Common features will be described briefly, or a description thereof will be omitted. FIG. 19A is a plan view schematically showing a gas sensor according to embodiment 11. FIG. 19B is a side view schematically showing the detectors and optical filters that the gas sensor according to embodiment 11 is provided with. In FIG. 19A, illustration of the light reflecting part 108 and the lid member 118 is omitted.

The gas sensor 100 (100E) according to this embodiment includes a light source 102, a detector 104, a light passage 106, a light reflecting part 108 (see FIG. 10), a lid member 118 (see FIG. 10), and a plurality of optical filters 126a, 126b. The detector 104 includes a plurality of detection units 104c, 104d. Each of the detection unit 104c and the detection unit 104d is a light receiving device. It is preferable that the detection unit 104c and the detection unit 104d are provided at positions symmetric with respect to a straight line passing through the center P2 of the light source 102 and the center P3 of the detector 104. The feature allows the detection unit 104c and the detection unit 104d to cancel the variation in light intensity caused by mechanical fluctuations in parts of the gas sensor 100 or the fluctuation in the output of the light source 102.

The plurality of optical filters 126a, 126b are provided to correspond to the plurality of detection units 104c, 104d, respectively. In this embodiment, the optical filter 126a is provided to correspond to the detection unit 104c, and the optical filter 126b is provided to correspond to the detection unit 104d. The optical filters are provided directly on the light receiving surfaces of the respective detection units or spaced apart therefrom. The optical filters 126a, 126b are optical members that cause the light of a predetermined wavelength to be incident selectively on the corresponding detection units 104c, 104d. In other words, the optical filters 126a, 126b transmit only the light of a predetermined wavelength, and the light transmitted through the optical filters 126a, 126b is incident on the detection units 104c, 104d.

Of the plurality of optical filters, one or more optical filters transmit the light of a predetermined wavelength absorbed by the gas subject to detection, and the remaining one or more optical filters transmit the light of a wavelength different from the wavelength that said some optical filters transmit.

In this embodiment, optical filter 126a transmits the light of a wavelength 4.26 μm absorbed by $CO_2$, and the optical filter 126b transmits the light of a wavelength 3.91 μm, by way of example. The detection unit 104d of the gas sensor 100 detects the variation in the intensity of the light of the wavelength 3.91 μm. The gas sensor 100 detects the presence and density of $CO_2$ based on the variation in the intensity of the light of the wavelength 4.26 μm detected by the detection unit 104c and the result of detection by the detection unit 104d.

The light of the wavelength 3.91 μm is used as a reference light. The variation in the intensity of light caused by external disturbance other than the absorption of light by the gas subject to detection is detected by learning the variation in the intensity of light of the wavelength 3.91 μm. Thus, by using some detection units to detect the variation in the intensity of reference light and using the detection result for the detection of the gas subject to detection, the gas subject to detection is detected with a higher accuracy. The detection unit 104c and the detection unit 104d may be configured to detect different gases subject to detection. The feature allows a single gas sensor 100 to detect a plurality of types of gas subject to detection. The detector 104 may include three or more detection units and optical filters.

Embodiment 12

Figure 20:
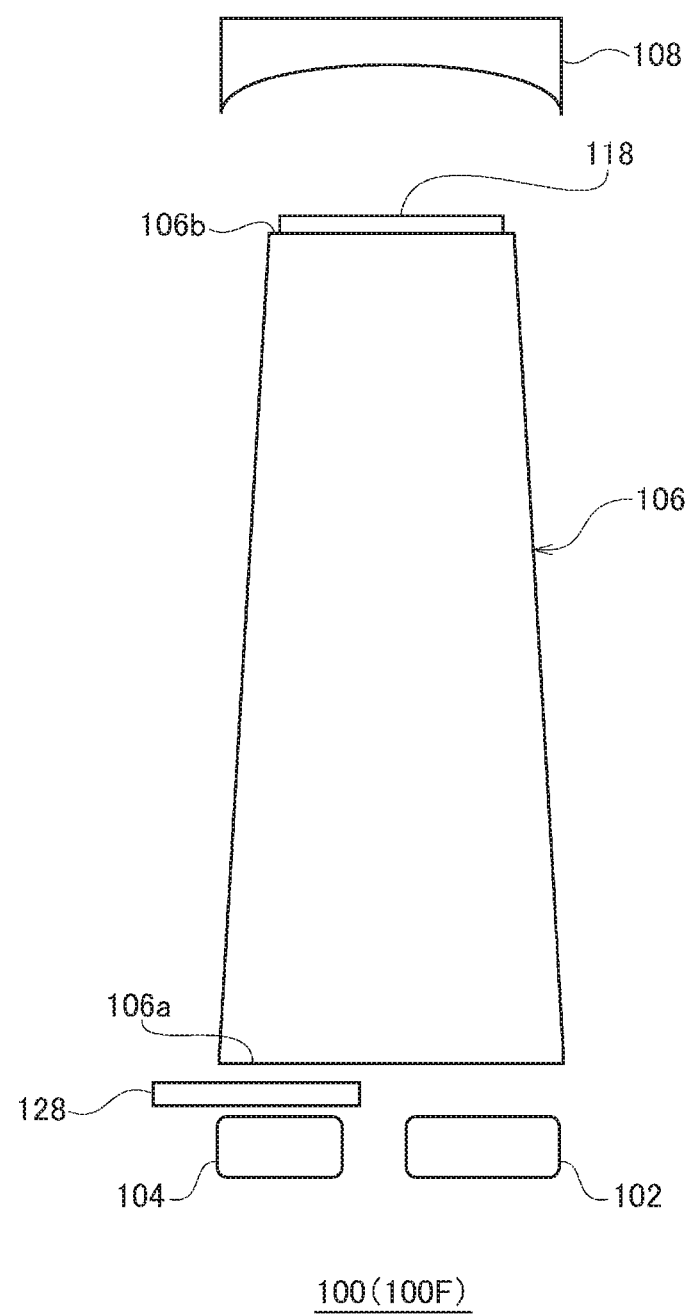
FIG. 20 is a side view schematically showing a gas sensor according to embodiment 12.

The gas sensor according to embodiment 12 has a configuration which is common to that of embodiment 7 except that an optical filter is provided on the light receiving surface of the detector 104. Those features of the gas sensor according to this embodiment that are different from those of embodiment 7 will mainly be described. Common features will be described briefly, or a description thereof will be omitted. FIG. 20 is a side view schematically showing a gas sensor according to embodiment 12.

The gas sensor 100 (100F) according to this embodiment includes a light source 102, a detector 104, a light passage 106, a light reflecting part 108, a lid member 118, and an optical filter 128. The optical filter 128 is an optical member that causes the light of a predetermined wavelength to be incident selectively on the detector 104. For example, the optical filter 128 transmits the light of a wavelength 4.26 μm absorbed by $CO_2$, i.e., the gas subject to detection. As a result, the light of the wavelength 4.26 μm is selectively caused to be incident on the detector 104. This improves the accuracy of detection by the gas sensor 100.

The optical filter 128 according to this embodiment may be a variable wavelength filter in which the band of transmitted wavelength is variable. The feature allows a single gas sensor 100 to detect a plurality of types of gas subject to detection. By using the light of a predetermined wavelength as a reference light and detecting the variation in its intensity, the gas subject to detection is detected with a higher accuracy.

The embodiments and variations of the present invention are not limited to those described above and the embodiments and variations may be combined, or various further modifications such as design changes may be made based on the knowledge of a skilled person. The embodiments and variations resulting from such combinations or further modification are also within the scope of the present invention. New embodiments created by combinations of the above-described embodiments and variations and new embodiments created by further modifications to the embodiments and variations provide combined advantages from the embodiments, variations, and further modifications.

The constant-temperature apparatus 1 according to the embodiments and variations described above is exemplified by a $CO_2$ incubator but may be another apparatus so long as the constant-temperature apparatus 1 is provided with a constant-temperature tank 4 filled the gas subject to detection. The gas sensor 100 according to the embodiments and variations described above can be suitably used to measure the density of gas in a high-temperature environment. For example, the gas sensor 100 can be used to measure exhaust gas, combustion gas, etc.

The gas subject to detection may be a gas other than $CO_2$ and $H_2O$. Other gases subject to detection may include sulfur dioxide ($SO_2$, absorption wavelength: 7.3 μm, 7.35 μm), sulfur trioxide ($SO_3$, absorption wavelength: 7.25 μm, 7.14 μm), nitric monoxide (NO, absorption wavelength: 5.3 μm, 5.5 μm), carbon monoxide (CO, absorption wavelength: 4.2 μm), nitrogen monoxide ($N_2O$, absorption wavelength: 4 μm, 4.5 μm, 7.9 μm), nitrogen dioxide ($NO_2$, absorption wavelength, 5.7 μm, 6.3 μm), etc.

In embodiments 1~6, an optical filter may be provided in the detector 104 as in embodiments 11, 12. The optical filter is an optical member that causes the light of a predetermined wavelength to be incident selectively on the detector 104. The wavelength selectively transmitted by the optical filter may be determined in accordance with the type of gas subject to detection. For example, the optical filter may transmit the light of a wavelength 4.26 μm absorbed by $CO_2$, i.e., the gas subject to detection. As a result, the light of the wavelength 4.26 μm is selectively caused to be incident on the detector 104. This improves the accuracy of detection by the gas sensor 100.

The optical filter 128 may be a variable wavelength filter in which the band of transmitted wavelength is variable. The feature allows a single gas sensor 100 to detect a plurality of types of gas subject to detection. Further, by using the light of a predetermined wavelength as a reference light, detecting the variation in its intensity, and using the detection result for detection of the gas subject to detection, the gas subject to detection is detected with a higher accuracy.

The detector 104 may be provided with a plurality of detection units (light receiving devices), and the detection units may be provided with optical filter that transmit the light of different wavelengths. The feature allows a single gas sensor 100 to detect a plurality of types of gas subject to detection. Further, by using some detection units to detect the variation in the intensity of reference light and using the detection result for detection of the gas subject to detection by the other detection units, the gas subject to detection is detected with a higher accuracy.

In embodiments 7~12, the light passage 106 may be a solid body. The feature eliminates the need for the lid members 118, 122. In this case, the light passage 106 is, like the lid member 118, preferably made of a material that transmits the light emitted by the light source 102 (e.g., germanium, silicon, sapphire, etc. that are transmissive to infrared light).

What is claimed is:

1. A gas sensor comprising:
   a gas detection unit that includes a light source configured to emit light of a predetermined wavelength toward a gas subject to detection, and a detector that receives the light and detects the gas subject to detection based on absorption of the light by the gas subject to detection; and
   a gas passage that includes a first end, a second end opposite to the first end, and a hollow part extending from the first end to the second end, the first end being provided toward the gas detection unit, the second end being provided toward a gas space where the gas subject to detection is located, and the gas passage being configured to communicate the gas subject to detection between the gas space and the gas detection unit via the hollow part, wherein
   the hollow part has a shape in which a cross-sectional area of a flow passage grows smaller away from the second end and toward the first end either in steps or continuously,
   the gas passage includes:
   a partition member that divides the hollow part into at least two areas including a first area and a second area each extending from the first end side to the second end side, respectively;
   a gas inflow port provided at the second end to connect the gas space to the first area; and
   a gas outflow port provided at the second end to connect the second area to the gas space, wherein
   the gas subject to detection located in the gas space flows from the gas inflow port into the hollow part, flows in the first area toward the first end, and arrives at the gas detection unit, and the gas subject to detection located in the gas detection unit flows in the second area toward the second end and flows out from the gas outflow port to the gas space.

2. The gas sensor according to claim 1, wherein the gas passage is provided to extend horizontally.

3. The gas sensor according to claim 2, wherein a lower surface of the hollow part in a perpendicular direction is sloped so as to descend in the perpendicular direction away from the first end and toward the second end.

4. The gas sensor according to claim 1, wherein an aperture area of the gas inflow port is larger than that of the gas outflow port.

5. The gas sensor according to claim 1, wherein the gas inflow port is provided upstream in a flow of the gas subject to detection in the gas space, and the gas outflow port is provided downstream of the gas inflow port in the flow of the gas subject to detection.

6. The gas sensor according to claim 1, further comprising:
a straightener that projects from an area at the second end between the gas inflow port and the gas outflow port into the gas space to restrict a flow of the gas subject to detection in the gas space.

7. The gas sensor according to claim 1, wherein the light source and the detector are provided such that a light emitting surface of the light source and a light receiving surface of the detector face each other.

8. The gas sensor according to claim 1, wherein the light source is provided below the detector in a perpendicular direction, and the gas inflow port is provided below the gas outflow port in the perpendicular direction.

9. The gas sensor according to claim 1, wherein the gas detection unit includes:
a gas introduction chamber through which the gas subject to detection flows in;
a first housing provided adjacent to the gas introduction chamber and housing the light source;
a second housing provided adjacent to the gas introduction chamber and housing the detector;
a first lid member that transmits the light and spaces the gas introduction chamber and the first housing apart from each other; and
a second lid member that transmits the light and spaces the gas introduction chamber and the second housing apart from each other.

10. The gas sensor according to claim 1, wherein the gas passage is made of an adiabatic material at least in part.

* * * * *